(12) United States Patent
Prag

(10) Patent No.: US 11,932,846 B2
(45) Date of Patent: Mar. 19, 2024

(54) CHLORAMPHENICOL RESISTANT SPLIT PROTEIN AND USES THEREOF

(71) Applicant: Technology Innovation Momentum Fund (Israel) Limited Partnership, Tel-Aviv (IL)

(72) Inventor: Gali Prag, Tel-Aviv (IL)

(73) Assignee: Technology Innovation Momentum Fund (Israel) Limited Partnership, Tel-Aviv (IL)

( * ) Notice: Subject to any disclaimer, the term of this patent is extended or adjusted under 35 U.S.C. 154(b) by 1056 days.

(21) Appl. No.: 16/634,898

(22) PCT Filed: Aug. 8, 2018

(86) PCT No.: PCT/IL2018/050880
§ 371 (c)(1),
(2) Date: Jan. 29, 2020

(87) PCT Pub. No.: WO2019/030759
PCT Pub. Date: Feb. 14, 2019

(65) Prior Publication Data
US 2020/0385706 A1  Dec. 10, 2020

Related U.S. Application Data

(60) Provisional application No. 62/542,333, filed on Aug. 8, 2017.

(51) Int. Cl.
*C12N 15/10* (2006.01)
*C12N 15/03* (2006.01)
(Continued)

(52) U.S. Cl.
CPC ......... *C12N 15/1055* (2013.01); *C12N 15/03* (2013.01); *C12Q 1/025* (2013.01);
(Continued)

(58) Field of Classification Search
CPC .. C12N 15/1055; C12N 15/03; C12N 9/1033; C12Q 1/025; C12Q 1/48;
(Continued)

(56) References Cited

U.S. PATENT DOCUMENTS 10,982,252 B2  4/2021  Prag
2002/0025569 A1  2/2002  Caligiuri
(Continued)

FOREIGN PATENT DOCUMENTS

WO  WO 2013/112625  8/2013
WO  WO 2017/201449  11/2017
(Continued)

OTHER PUBLICATIONS

Leslie et al., Proc. Nail. Acad. Sci., 1988, 85: 4133-4137 (Year: 1988).*
(Continued)

*Primary Examiner* — Allison M Fox
*Assistant Examiner* — Qing Xu
(74) *Attorney, Agent, or Firm* — COOLEY LLP; Ivor R. Elrifi

(57) ABSTRACT

A system for expressing a chloramphenicol split protein is disclosed. Uses thereof are also disclosed.

14 Claims, 10 Drawing Sheets
(10 of 10 Drawing Sheet(s) Filed in Color)
Specification includes a Sequence Listing.

(51) Int. Cl.
*C12Q 1/02* (2006.01)
*C12Q 1/48* (2006.01)

(52) U.S. Cl.
CPC ........ *C12Q 1/48* (2013.01); *C12Y 203/01028* (2013.01); *G01N 2333/91062* (2013.01); *G01N 2500/02* (2013.01)

(58) Field of Classification Search
CPC . C12Y 203/01028; G01N 2333/91062; G01N 2500/02
See application file for complete search history.

(56) References Cited

U.S. PATENT DOCUMENTS

| | | | |
|---|---|---|---|
| 2003/0049688 | A1 | 3/2003 | Michnick et al. |
| 2004/0043386 | A1 | 3/2004 | Pray et al. |
| 2006/0194262 | A1 | 8/2006 | Xu et al. |
| 2007/0059731 | A1 | 3/2007 | Kerppola |
| 2009/0298089 | A1 | 12/2009 | Rossner et al. |
| 2011/0287963 | A1* | 11/2011 | Delisa ............... C12N 15/1055 435/6.1 |
| 2017/0275341 | A1 | 9/2017 | Zhang |
| 2019/0185902 | A1 | 6/2019 | Prag |
| 2021/0269845 | A1 | 9/2021 | Prag |
| 2021/0356467 | A1 | 11/2021 | Prag |

FOREIGN PATENT DOCUMENTS

| | | |
|---|---|---|
| WO | WO 2018/029682 | 2/2018 |
| WO | WO 2019/030759 | 2/2019 |
| WO | WO 2020/079687 | 4/2020 |

OTHER PUBLICATIONS

Alton et al., Nature, 1979, 282: 864-869 and the printout (Year: 1979).*

Wehrman et al., Proc. Nail. Acad. Sci., 2002, 99:3469-3474 (Year: 2002).*

The printout of pUC19 map, downloaded on May 6, 2023 from https://www.neb.com/products/n3041-puc19-vector#Product%20Information (Year: 2023).*

Supplementary European Search Report and the European Search Opinion dated Jun. 22, 2022 From the European Patent Office Re. Application No. 19874374.2. (8 pages).

Collins et al. "Chemical Approaches to Targeted Protein Degradation through Modulation of the Ubiquitin-proteasome Pathway", Biochemical Journal, 474(7): 1127-1147, Mar. 15, 2017.

Restriction Official Action dated Aug. 27, 2020 from the US Patent and Trademark Office Re. U.S. Appl. No. 16/322,956. (4 pages).

Notice of Allowance dated Dec. 8, 2020 From the US Patent and Trademark Office Re. U.S. Appl. No. 16/322,956. (17 Pages).

Chakraborty et al. "The E3 Ubiquitin Ligase Trim7 Mediates C-Jun/AP-1 Activation by Ras Signalling", Nature Communications, 6(1): 6782-1-6782-12, Apr. 8, 2015.

International Preliminary Report on Patentability dated Feb. 21, 2019 From the International Bureau of WIPO Re. Application No. PCT/IL2017/050876. (11 Pages).

International Search Report and the Written Opinion dated Jan. 12, 2020 From the International Searching Authority Re. Application No. PCT/IL2019/051122. (14 Pages).

International Search Report and the Written Opinion dated Nov. 13, 2018 From the International Searching Authority Re. Application No. PCT/IL2018/050880. (12 Pages).

International Search Report and the Written Opinion dated Oct. 25, 2017 From the International Searching Authority Re. Application No. PCT/IL2017/050876. (20 Pages).

Chen et al. "Random Dissection to Select for Protein Split Sites and Its Application in Protein Fragment Complementation", Protein Science, 18(2): 399-409, Published Online Dec. 29, 2008. Figs. 1, 2.

Ciechanover et al. "The Ubiquitin Proteasome System in Neurodegenerative Diseases: Sometimes the Chicken, Sometimes the Egg", Neuron, 40(2): 427-446, Oct. 9, 2003. p. 430, Right Col., 2nd Para-p. 434, Right Col., Last Para, p. 436, Left Col., 2nd Para.

Keren-Kaplan et al. "Purification and Crystallization of Mono-Ubiquitylated Ubiquitin Receptor Rpn10", Acta Crystallographica Section F, F68(9): 1120-1123, Sep. 1, 2012.

Keren-Kaplan et al. "Synthetic Biology Approach to Reconstituting the Ubiquitylation Cascade in Bacteria", The EMBO Journal, 31(2): 378-390, Published Online Nov. 11, 2011. p. 378, First Para-p. 379, First Para, p. 381, Left Col., 2nd Para, p. 386, Left Col., Last Para, Fig. 1.

Keren-Kaplan et al. "Synthetic Biology Approach to Reconstituting the Ubiquitylation Cascade in Bacteria", The EMBO Journal, Supplementary Material, p. 1-28, 2011.

Levin-Kravets et al. "A Bacterial Genetic Selection System for Ubiquitylation Cascade Discovery", Nature Methods, 13(11): 945-952, Published Online Oct. 3, 2016. Abstract, p. 945, Left Col., First Para-p. 946, Right Col., First Para, Figs. 1, 4.

Levin-Kravets et al. "A Bacterial Genetic Selection System for Ubiquitylation Cascade Discovery", Nature Methods, Supplementary Materials, 11 P., Published Online Oct. 3, 2016.

Levin-Kravets et al. "*E. coli*-Based Selection and Expression Systems for Discovery, Characterization, and Purification of Ubiquitylated Proteins", The Ubiquitin Proteasome System: Methods and Protocols, Methods in Molecular Biology, 1844(Chap. 11): 155-166, Sep. 22, 2018.

Miao et al. "A HECT E3 Ubiquitin Ligase Negatively Regulates *Arabidopsis* Leaf Senescence Through Degradation of the Transcription Factor WRKY53", The Plant Journal, 63(2): 179-188, Published Online May 11, 2010. p. 180, Last Para-p. 181, Right Col., First Para, Fig. 1d, 1e, p. 187, Left Col., 2nd Para-Right Col., 2nd Para.

Roxburgh et al. "Small Molecules That Bind the Mdm2 RING Stabilize and Activate P53", Carcinogenesis, 33(4): 791-798, Published Online Feb. 2, 2012. p. 792, Left Col., Last Para, p. 794, Left Col., Last Para, Figs.4A.

Shekhawat et al. "Split-Protein Systems: Beyond Binary Protein-Protein Interactions", Current Opinion in Chemical Biology, 15(6): 789-797, Available Online Nov. 7, 2011. Abstract, p. 2, First Para.

Su et al. "A Novel E3 Ubiquitin Ligase Substrate Screen Identifies Rho Guanine Dissociation Inhibitor as A Substrate of Gene Related to Anergy in Lymphocytes", The Journal of Immunology, 177(11): 7559-7566, Dec. 2006.

Official Action dated Jan. 31, 2023 from the US Patent and Trademark Office Re. U.S. Appl. No. 17/207,943. (16 pages).

Stagljar et al. "A Genetic System Based on Split-Ubiquitin for the analysis of Interactions Between Membrane Proteins in Vivo", PNAS, 95(9): 5187-5192, Apr. 28, 1998.

Verma "Split Beta-Lactamase Complementation Assay", Resonance, 20:816-821, Oct. 15, 2015.

Supplementary European Search Report and the European Search Opinion dated Mar. 17, 2020 From the European Patent Office Re. Application No. 17838924.3. (10 Pages).

Maculins et al. "A Generic Platform for Cellular Screening Against Ubiquitin Ligases", Scientific Reports, XP055673723, 6(1): 18940-1-18940-10, Published Online Jan. 8, 2016.

Official Action dated Aug. 1, 2023 from the US Patent and Trademark Office Re. U.S. Appl. No. 17/207,943 (12 pages).

* cited by examiner

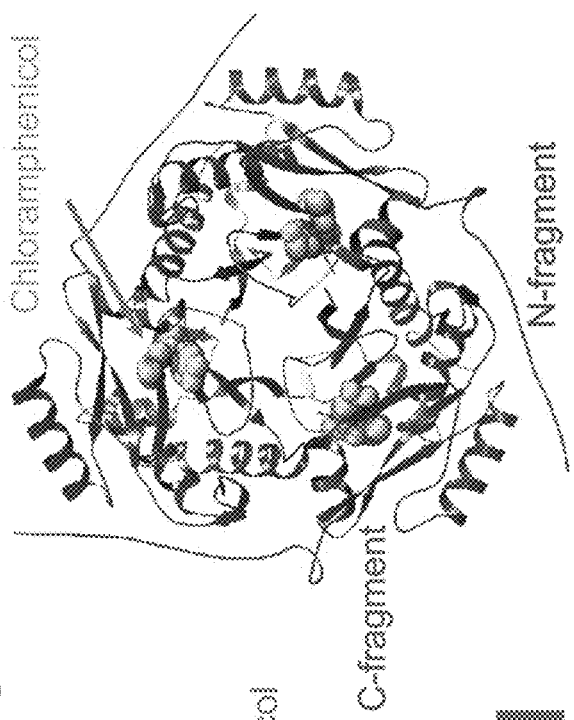
FIG. 2A
FIG. 2B
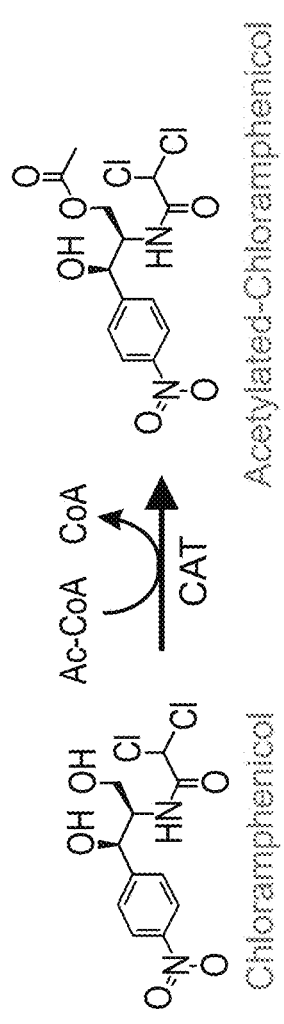
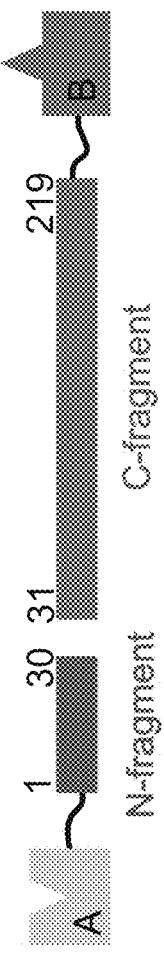
FIG. 2C

FIG. 8A

```
  1 M E K K I T G Y T T V D I S Q W H R K E  20
  1 ATGGAGAAAAAAATCACTGGATATACCACCGTTGATATATCCCAATGGCATCGTAAAGAA 60
```

Cleavage site 

```
 21 H F E A F Q S V A Q C T Y N Q T V Q L D  40
 61 CATTTTGAGGCATTTCAGTCAGTTGCTCAATGTACCTATAACCAGACCGTTCAGCTGGAT 120

41 I T A F L K T V K K N K H K F Y P A F I  60
121 ATTACGGCCTTTTTAAAGACCGTAAAGAAAAATAAGCACAAGTTTTATCCGGCCTTTATT 180

61 H I L A R L M N A H P E F R M A M K D G  80
181 CACATTCTTGCCCGCCTGATGAATGCTCATCCGGAATTCCGTATGGCAATGAAAGACGGT 240

81 E L V I W D S V H P C Y T V F H E Q T E 100
241 GAGCTGGTGATATGGGATAGTGTTCACCCTTGTTACACCGTTTTCCATGAGCAAACTGAA 300

101 T F S S L W S E Y H D D F R Q F L H I Y 120
301 ACGTTTTCATCGCTCTGGAGTGAATACCACGACGATTTCCGGCAGTTTCTACACATATAT 360

121 S Q D V A C Y G E N L A Y F P K G F I E 140
361 TCGCAAGATGTGGCGTGTTACGGTGAAAACCTGGCCTATTTCCCTAAAGGGTTTATTGAG 420

141 N M F F V S A N P W V S F T S F D L N V 160
421 AATATGTTTTTCGTCTCAGCCAATCCCTGGGTGAGTTTCACCAGTTTTGATTTAAACGTG 480

161 A N M D N F F A P V F T M G K Y Y T Q G 180
481 GCCAATATGGACAACTTCTTCGCCCCCGTTTTCACCATGGGCAAATATTATACGCAAGGC 540

181 D K V L M P L A I Q V H H A V C D G F H 200
541 GACAAGGTGCTGATGCCGCTGGCGATTCAGGTTCATCATGCCGTCTGTGATGGCTTCCAT 600

201 V G R M L N E L Q Q Y C D E W Q G G A * 220
601 GTCGGCAGAATGCTTAATGAATTACAACAGTACTGCGATGAGTGGCAGGGCGGGGCGTAA 660
```

FIG. 8B

```
  1  M  E  K  K  I  T  G  Y  T  T  V  D  I  S  Q  W  H  R  K  E  20
  1  ATGGAGAAAAAATCACTGGATATACCACCGTTGATATATCCCAATGGCATCGTAAAGAA 60

21  H  F  E  A  F  Q  S  V  A  Q  *  30                    N-fragment
 61  CATTTTGAGGCATTTCAGTCAGTTGCTCAATAA 94

1  M  C  T  Y  N  Q  T  V  Q  L  D  11                    C-fragment
  1  ATGTGTACCTATAACCAGACCGTTCAGCTGGAT 33

12  I  T  A  F  L  K  T  V  K  K  N  K  H  K  F  Y  P  A  F  I  31
 34  ATTACGGCCTTTTTAAAGACCGTAAAGAAAAATAAGCACAAGTTTTATCCGGCCTTTATT 93

32  H  I  L  A  R  L  M  N  A  H  P  E  F  R  M  A  M  K  D  G  51
 94  CACATTCTTGCCCGCCTGATGAATGCTCATCCGGAATTCCGTATGGCAATGAAAGACGGT 153

52  E  L  V  I  W  D  S  V  H  P  C  Y  T  V  F  H  E  Q  T  E  71
154  GAGCTGGTGATATGGGATAGTGTTCACCCTTGTTACACCGTTTTCCATGAGCAAACTGAA 213

72  T  F  S  S  L  W  S  E  Y  H  D  D  F  R  Q  F  L  H  I  Y  91
214  ACGTTTTCATCGCTCTGGAGTGAATACCACGACGATTTCCGGCAGTTTCTACACATATAT 273

92  S  Q  D  V  A  C  Y  G  E  N  L  A  Y  F  P  K  G  F  I  E  111
274  TCGCAAGATGTGGCGTGTTACGGTGAAAACCTGGCCTATTTCCCTAAAGGGTTTATTGAG 333

112  N  M  F  F  V  S  A  N  P  W  V  S  F  T  S  F  D  L  N  V  131
334  AATATGTTTTTCGTCTCAGCCAATCCCTGGGTGAGTTTCACCAGTTTTGATTTAAACGTG 393

132  A  N  M  D  N  F  F  A  P  V  F  T  M  G  K  Y  Y  T  Q  G  151
454  GCCAATATGGACAACTTCTTCGCCCCCGTTTTCACCATGGGCAAATATTATACGCAAGGC 453

152  D  K  V  L  M  P  L  A  I  Q  V  H  H  A  V  C  D  G  F  H  171
514  GACAAGGTGCTGATGCCGCTGGCGATTCAGGTTCATCATGCCGTCTGTGATGGCTTCCAT 513

172  V  G  R  M  L  N  E  L  Q  Q  Y  C  D  E  W  Q  G  G  A  *  190
574  GTCGGCAGAATGCTTAATGAATTACAACAGTACTGCGATGAGTGGCAGGGCGGGGCGTAA 573
```

| | | | |
|---|---|---|---|
| EDS05563 | AFQSVA TYNQTVQLDI | WP_023148559 | AFQSVA TYNQTVQLDI |
| WP_080619625 | AFQSVA TYNQTVQLDI | WP_050436713 | AFQSVA TYNQTVQLDI |
| ADC79570 | AFQSVA TYNQTVQLDI | WP_080627472 | AFQSVA TYNQTVQLDI |
| BBB37551 | AFQSVA TYNQTVQLDI | WP_063695096 | AFQSVA TYNQTVQLDI |
| KLX70575 | AFQSVA TYNQTVQLDI | WP_080613016 | AFQSVA TYNQTVQLDI |
| ETE06580 | AFQSVA TYNQTVQLDI | ALP68362 | AFQSVA TYNQTVQLDI |
| WP_000412211 | AFQSVA TYNQTVQLDI | BAF44955 | AFQSVA TYNQTVQLDI |
| WP_002210545 | AFQSVA TYNQTVQLDI | WP_079665305 | AFQSVA TYNQTVQLDI |
| EDM85215 | AFQSVA TYNQTVQLDI | ANN45758 | AFQSVA TYNQTVQLDI |
| WP_063843217 | AFQSVA TYNQTVQLDI | AAA57080 | AFQSVA TYNQTVQLDI |
| ACI41886 | AFQSVA TYNQTVQLDI | WP_058647359 | AFQSVA TYNQTVQLDI |
| WP_097344126 | AFQSVA TYNQTVQLDI | WP_113974445 | AFQSVA TYNQTVQLDI |
| WP_087449280 | AFQSVA TYNQTVQLDI | WP_080624605 | AFQSVA TYNQTVQLDI |
| SRQ78057 | AFQSVA TYNQTVQLDI | WP_099562397 | AFQSVA TYNQTVQLDI |
| WP_049194493 | AFQSVA TYNQTVQLDI | WP_080612731 | AFQSVA TYNQTVQLDI |
| WP_006286297 | AFQSVA TYNQTVQLDI | KZP38921 | AFQSVA TYNQTVQLDI |
| AAK94926 | AFQSVA TYNQTVQLDI | WP_021553079 | AFQSVA TYNQTVQLDI |
| CAP45367 | AFQSVA TYNQTVQLDI | AAF86675 | AFQSVA TYNQTVQLDI |
| WP_063160494 | AFQSVA TYNQTVQLDI | WP_002437842 | AFQSVA TYNQTVQLDI |
| ACL01111 | AFQSVA TYNQTVQLDI | BAA03490 | AFQSVA TYNQTVHLDI |
| WP_029402709 | AFQSVA TYNQTVQLDI | WP_029676039 | AFQSVA TYNQTVQLDI |
| WP_031942326 | AFQSVA TYNQTVQLDI | WP_107764245 | AFQSVA TYNQTVQLDI |
| WP_112013353 | AFQSVA TYNQTVQLDI | WP_063843218 | AFQSVA TYNQTVQLDI |
| WP_011152976 | AFQSVA TYNQTVQLDI | BAM71968 | AFQSVA TYNQTVQLDI |
| AJW82936 | AFQSVA TYNQTVQLDI | CAA49282 | AFQSVA TYNQTVQLDI |
| AJW32929 | AFQSVA TYNQTVQLDI | WP_036088245 | AFQSVA TYNQTVQLDI |
| AAG41774 | AFQSVA TYNQTVQLDI | AST09971 | AFQSVA TYNQTVQLDI |
| ABK62679 | AFQSVA TYNQTVQLDI | AKV89136 | AFQSVA TYNQTVQLDI |
| WP_005637780 | AFQSVA TYNQTVQLDI | EJD67136 | AFQSVA TYNQTVQLDI |
| WP_044925362 | AFQSVA TYNQTVQLDI | WP_080942648 | AFQSVA TYNQTVQLDI |
| WP_111947031 | AFQSVA TYNQTVQLDI | ALV82398 | AFQSVA TYNQTVQLDI |
| AAC53603 | AFQSVA TYNQTVQLDI | AAT68191 | AFQSVA TYNQTVQLDI |
| WP_109917773 | AFQSVA TYNQTVQLDI | ADJ00052 | AFQSVA TYNQTVQLDI |
| WP_079693192 | AFQSVA TYNQTVQLDI | WP_089591712 | AFQSVA TYNQTVQLDI |
| WP_079448887 | AFQSVA TYNQTVQLDI | WP_113798109 | AFQSVA TYNQTVQLDI |
| P58777 | AFQSVA TYNQTVQLDI | WP_073056922 | AFQSVA TYNQTVQLDI |
| BAV44483 | AFQSVA TYNQTVQLDI | WP_032424446 | AFQSVA TYNQTVQLDI |
| WP_079733231 | AFQSVA TYNQTVQLDI | WP_096952516 | AFQSVA TYNQTVQLDI |
| WP_068815675 | AFQSVA TYNQTVQLDI | WP_101344820 | AFQSVA TYNQTVQLDI |
| BAH70333 | AFQSVA TYNQTVQLNI | WP_085862478 | AFQSVA TYNQTVQLDI |
| WP_079707575 | AFQSVA TYNQTVQLDI | WP_079877697 | AFQSVA TYNQTVQLDI |
| ADJ00045 | AFQSVA TYNQTVQLDI | WP_015420186 | AFQSVA TYNQTVQLDI |
| BAA03187 | AFQSVA TYNQTVQLDI | WP_063845422 | AFQSVA TYNQTVQLDI |
| WP_079846806 | AFQSVA TYNQTVQLDI | | |

US 11,932,846 B2

CHLORAMPHENICOL RESISTANT SPLIT PROTEIN AND USES THEREOF

RELATED APPLICATIONS

This application is a National Phase of PCT Patent Application No. PCT/IL2018/050880 having International filing date of Aug. 8, 2018, which claims the benefit of priority under 35 USC § 119(e) of U.S. Provisional Patent Application No. 62/542,333 filed on Aug. 8, 2017. The contents of the above applications are all incorporated by reference as if fully set forth herein in their entirety.

SEQUENCE LISTING STATEMENT

The ASCII file, entitled 80581SequenceListing.txt, created on Jan. 29, 2020, comprising 10,400 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to a chloramphenicol-resistant split protein and uses thereof.

Functional assembly of split reporter protein fragments is common methodology to study protein-protein interactions (PPI). The function of the reporter protein determines the downstream assay to assess or to screen the studied interaction(s). The reporters can be divided into two types based on their function: detection or selection. Example of a reporters for detection are a fluorescent protein or proteins that creates different colors that can be easily detected upon functional assembly. Examples of a reporters for selection include antibiotic-resistance or toxic proteins that facilitate selection of the desire PPI from a pool of gene products. In principle, one benefit of selection over detection split reporters is that it allows screening of rare PPI event in a very large number of cells ($\sim 10^9$). Several split antibiotic resistance systems have been developed such as split β-lactamase that allows selection with the bactericidal antibiotic penicillin and its derivatives. Other split antibiotic resistance proteins that have been developed include split DHFR (dihydrofolate reductase) which is based on resistance to a bacteriostatic antibiotic. DHFR is a key enzyme in the synthetic pathways of thymidine and several amino acids and therefore it becomes essential under conditions where one or few of these metabolites are missing or limited. Michnick and co-workers developed a split DHFR system to detect PPI (Pelletier et al., 1998, Proceedings of the National Academy of Sciences, 95(21), 12141-12146). Tethering protein partners to the split mammalian DHFR fragments gives rise to bacterial growth under restrictive conditions whereas the bacterial DHFR is inhibited by trimethoprim (a bacteriostatic antibiotic that selectively inhibits bacterial DHFR but not the mammalian DHFR). In eukaryotic cells methotrexate is used to inhibit the endogenous DHFR whereas the split mouse DHFR is insensitive to the drug due to a point mutation.

Background art includes US Application No. 20110287963.

SUMMARY OF THE INVENTION

According to an aspect of some embodiments of the present invention there is provided a construct system comprising:

(i) a first nucleic acid construct comprising a first polynucleotide having a nucleic acid sequence that encodes an N-terminal fragment of chloramphenicol acetyl transferase (CAT), the N-terminal fragment comprising a first portion of the catalytic active site of the CAT, the N-terminal fragment being devoid of acetylating activity; and (ii) a second nucleic acid construct comprising a second polynucleotide having a nucleic acid sequence that encodes a C terminal fragment of the CAT, the C-terminal fragment comprising a second portion of the catalytic active site of the CAT, the C-terminal fragment being devoid of acetylating activity; and wherein the N-terminal fragment is capable of associating with the C-terminal fragment to generate an active CAT that is capable of acetylating chloramphenicol.

According to an aspect of some embodiments of the present invention there is provided a cell which expresses:

(i) an N-terminal fragment of CAT comprising a first portion of the catalytic active site of the CAT; and (ii) a C-terminal fragment of the CAT, the C-terminal fragment comprising a second portion of the catalytic active site of the CAT, wherein the N-terminal fragment is not associated with the C-terminal fragment.

According to an aspect of some embodiments of the present invention there is provided a cell population which express the system of any one of claims 1-24.

According to an aspect of some embodiments of the present invention there is provided a cell culture comprising the cell population of claim 26 and a medium comprising chloramphenicol.

According to an aspect of some embodiments of the present invention there is provided a method of determining whether a first test polypeptide binds to a second test polypeptide comprising:

(a) expressing the system of claim 9 in a population of cells in a medium comprising chloramphenicol; and subsequently (b) analyzing survival of the cells, wherein the survival of a cell in the population of cells is indicative that the first test polypeptide has bound to the second test polypeptide in the cell.

According to an aspect of some embodiments of the present invention there is provided a method of identifying an agent which regulates the binding of a first test polypeptide to a second test polypeptide:

(a) contacting a population of cells with the agent, wherein the population of cells express an amount of active CAT which correlates with the binding of the first test polypeptide to the second test polypeptide; and (b) analyzing survival of the cells, wherein an increase or decrease in the survival of the cells as compared to the survival of the cells in the absence of the agent, is indicative of an agent which regulates the binding of the first test polypeptide to the second test polypeptide.

According to an aspect of some embodiments of the present invention there is provided an isolated polynucleotide comprising:

(i) a first nucleic acid sequence that encodes an N-terminal fragment of chloramphenicol acetyl transferase (CAT), wherein the first nucleic acid sequence comprises a stop codon positioned in the catalytic active site encoding sequence of the CAT; and (ii) a second nucleic acid sequence that encodes a C terminal fragment of the CAT, wherein the second nucleic acid sequence comprises a start codon positioned in the catalytic active site encoding sequence of the CAT, and wherein the N-terminal fragment is capable of associating with the C-terminal fragment to generate an active CAT that is capable of acetylating chloramphenicol.

According to some embodiments of the invention, the first polynucleotide and the second polynucleotide are operably linked to a regulatory sequence.

According to some embodiments of the invention, the regulatory sequence is a bacterial regulatory sequence.

According to some embodiments of the invention, the first polynucleotide further comprises a cloning site, wherein a position of the cloning site is selected such that upon insertion of a sequence which encodes a test polypeptide into the cloning site, following expression in a cell, a fusion protein is generated which comprises the test polypeptide in frame with the N-terminal fragment.

According to some embodiments of the invention, the second polynucleotide further comprises a cloning site, wherein a position of the cloning site is selected such that upon insertion of a sequence which encodes a test polypeptide into the cloning site, following expression in a cell, a fusion protein is generated which comprises the test polypeptide in frame with the C-terminal fragment.

According to some embodiments of the invention, the first and the second nucleic acid construct comprise a bacterial origin of replication.

According to some embodiments of the invention, the first nucleic acid construct further comprises a nucleic acid sequence that encodes a first test polypeptide at a position such that, following expression in a cell, a fusion protein is generated which comprises the test polypeptide in frame with the N-terminal fragment.

According to some embodiments of the invention, the second nucleic acid construct further comprises a nucleic acid sequence that encodes a second test polypeptide at a position such that, following expression in a cell, a fusion protein is generated which comprises the test polypeptide in frame with the C-terminal fragment.

According to some embodiments of the invention, the second nucleic acid construct further comprises a nucleic acid sequence that encodes a second test polypeptide, which is non-identical to the first test polypeptide, at a position such that, following expression in a cell, a second fusion protein is generated which comprises the second test polypeptide in frame with the C-terminal fragment.

According to some embodiments of the invention, the test polypeptide is ubiquitin.

According to some embodiments of the invention, the first nucleic acid construct or the second nucleic acid construct further encode at least one ubiquitinating enzyme.

According to some embodiments of the invention, the system further comprises a third nucleic acid construct having a nucleic acid sequence that encodes at least one ubiquitinating enzyme.

According to some embodiments of the invention, the test polypeptide which is in frame with the N-terminal fragment is non-identical to the test polypeptide with is in frame with the C-terminal fragment.

According to some embodiments of the invention, the test polypeptide is attached to the N-terminal fragment via a linker.

According to some embodiments of the invention, the test polypeptide is attached to the C-terminal fragment via a linker.

According to some embodiments of the invention, the N terminus of the N-terminal fragment is linked to the C terminus of the first test polypeptide in the fusion protein.

According to some embodiments of the invention, the C terminus of the C-terminal fragment is linked to the N terminus of the second test polypeptide in the fusion protein.

According to some embodiments of the invention, the first amino acid of the C terminal fragment is a small amino acid residue.

According to some embodiments of the invention, the N terminal fragment consists of the amino acid sequence as set forth in SEQ ID NO: 2 or 6.

According to some embodiments of the invention, the C-terminal fragment consists of the amino acid sequence as set forth in SEQ ID NOs: 3 or 7.

According to some embodiments of the invention, the active CAT comprises an amino acid sequence at least 90% homologous with SEQ ID NO: 1.

According to some embodiments of the invention, the first polynucleotide does not encode for more than 30 amino acids of the CAT.

According to some embodiments of the invention, the N-terminal fragment is encoded by the nucleic acid sequence as set forth in SEQ ID NO: 4.

According to some embodiments of the invention, the C-terminal fragment is encoded by the nucleic acid sequence as set forth in SEQ ID NO: 5.

According to some embodiments of the invention, the first test polypeptide or the second test polypeptide is ubiquitin.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawings will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
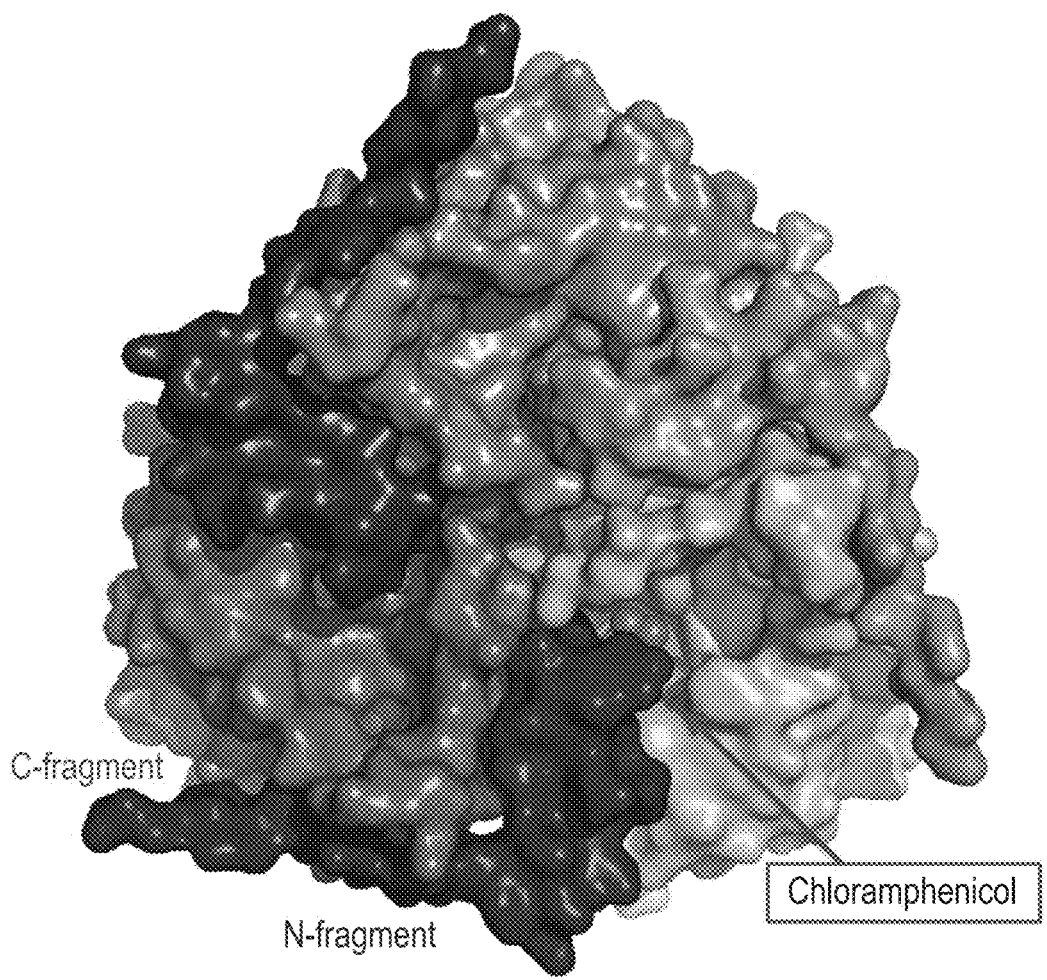

FIG. 1 Trimeric structure of CAT. The structure of $CAT_T$. Surface representation of the $CAT_T$:chloramphenicol complex (PDB code 3U9F) is shown. The enzyme functions as a homotrimer. Each protomer (light colors) harbors an active site pocket that is covered by the N-terminal fragment of the neighboring protomer (dark colors).

FIGS. 2A-C are schematic views of the split-CAT system.

A. The reaction executed by CAT (i.e. transfer of acetyl group from acetyl-CoA to chloramphenicol is shown.

B. Structure representation of assembled split CAT with chloramphenicol.

C. Linear representation of the split-CAT system.

Figure 3:
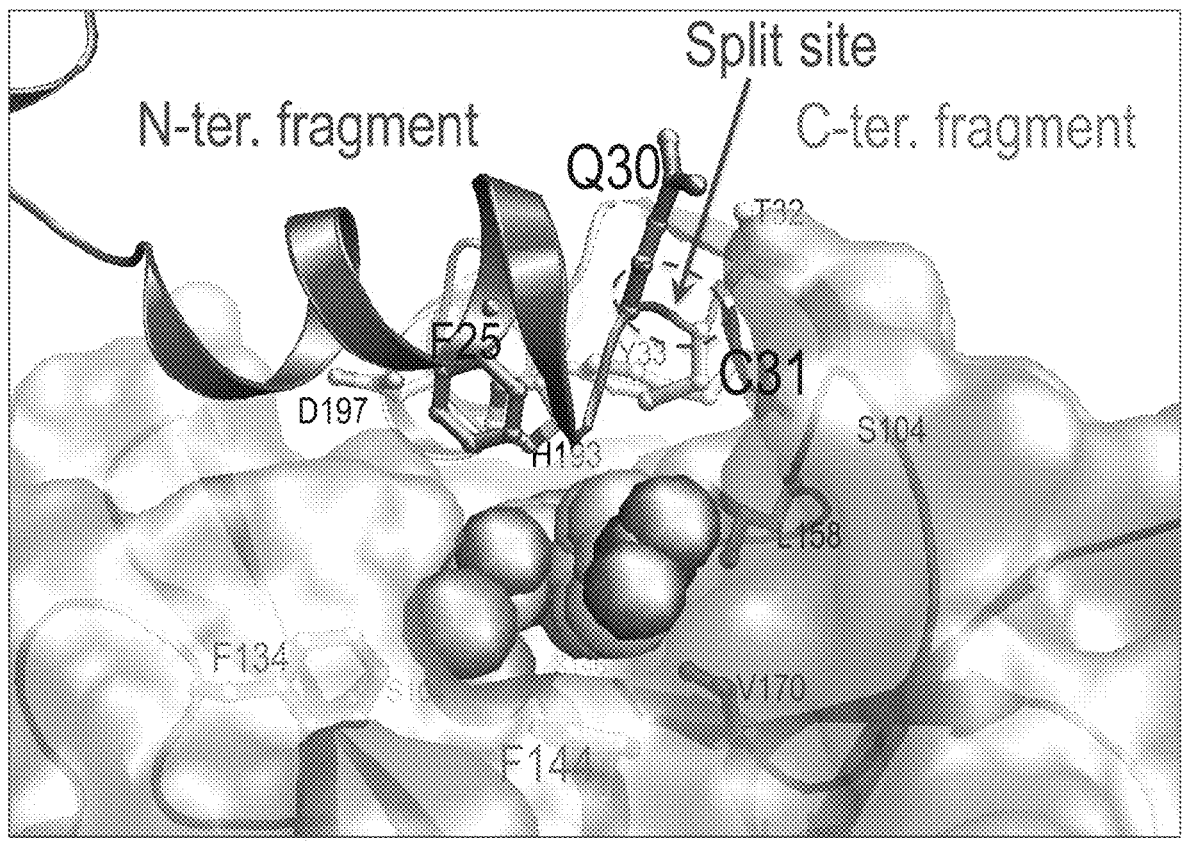

FIG. 3 is a structural representation of the CAT active site and the split site. The N-terminus fragment (a.a. 1-30) is shown in red. The C-terminus fragment residues 31-219 is shown in grey. Chloramphenicol (rendered in space-fill) is shown in the active site pocket of the enzyme. One protomer is rendered as surface to show the active site pocket. Critical residues which participate in substrate binding and catalysis are rendered in balls-and-sticks. The split site is circled with blue dashed line.

Figure 4A:
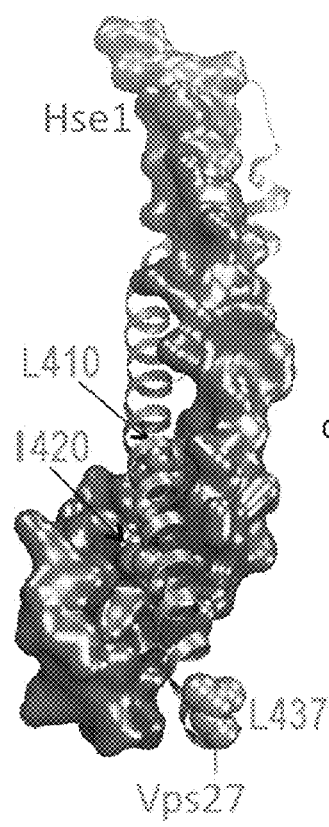
Figure 4B:
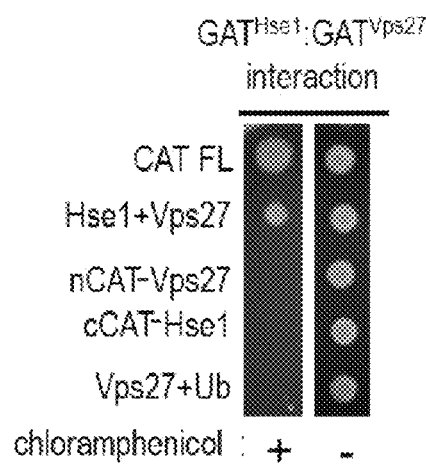
Figure 4C:
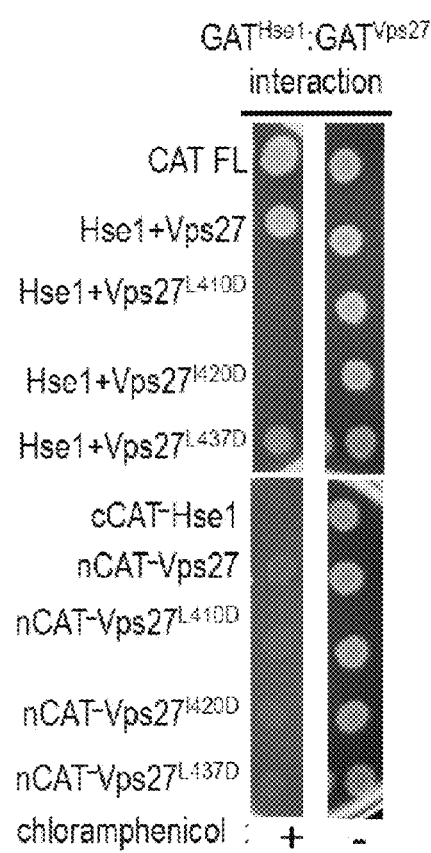

FIGS. 4A-C. The split-CAT system provides selection for Protein-Protein Interactions.

A. Shows the structure of the ESCRT-0 GAT domains complex. An intertwined coiled-coil hetro-complex structure shows some critical interacting residues (Prag et al Dev. Cell 2007).

B. Wild-type GAT domains show PPI in the Split-CAT system. Negative controls of only Vps27 or only Hse1 or against Ub do not show PPI.

C. Mutations (L410D and I420D) previously shown to abrogate the Vps27:Hse1 interaction shows growth phenotypes. L437D mutant which is not the PPI interface and predicted to not interfere with binding was used as positive control.

Figure 5:
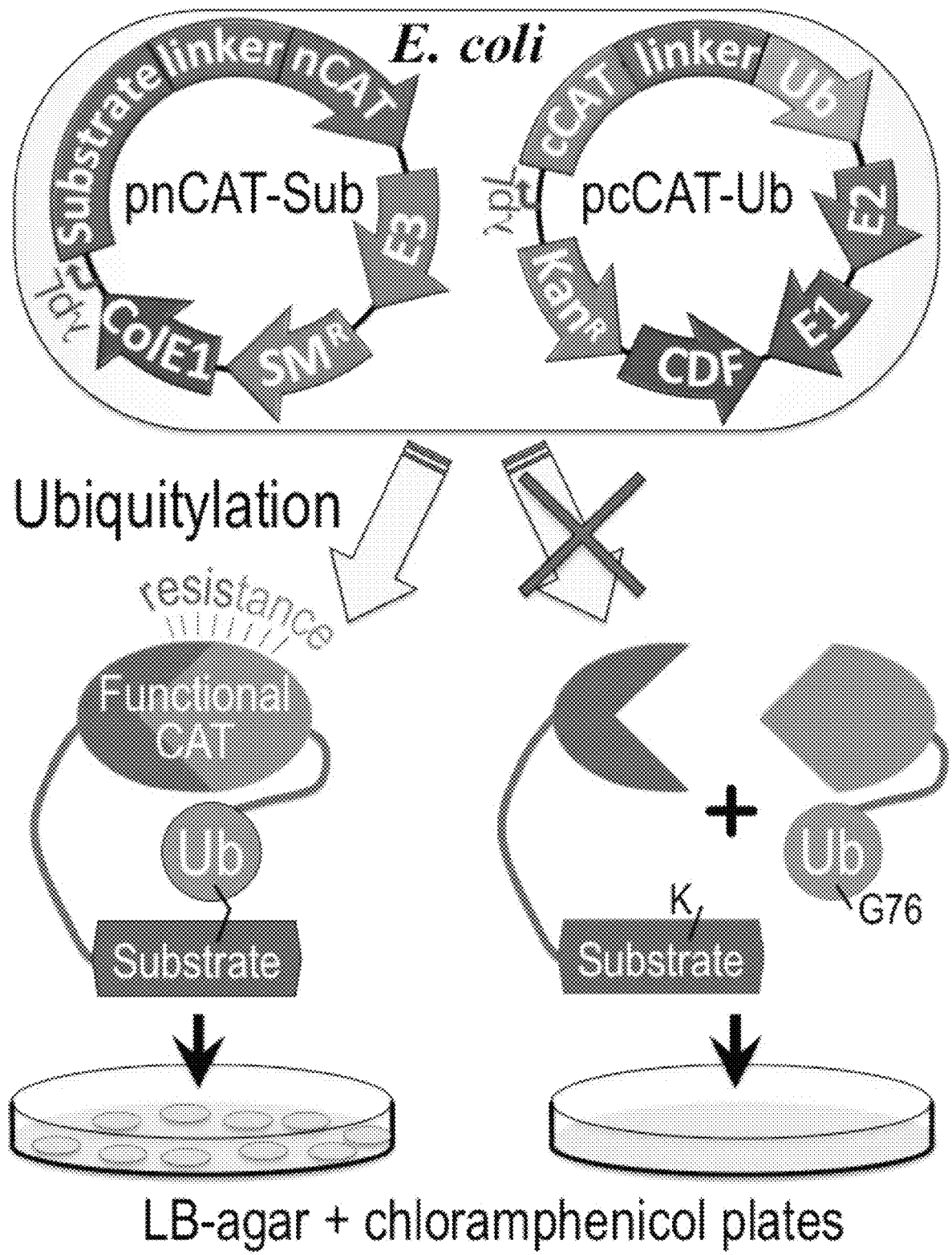

FIG. 5 is a schematic view of the split CAT bacterial selection system for ubiquitination.

FIGS. 6A-D. Split-CAT system detects ubiquitination.

A. Shows E3 independent uniquitination of the Ub-binding domain VHS of yeast Hse1.

B. The split CAT system shows significant higher growth efficiency that shortens the experimental time. Shown is UBE3A dependent ubiquitination of Rpn10 in the split CAT and DHFR selection system.

C. Mutation in UBE3A E3 ligase (G738E) that causes Angelman-syndrome phenotype.

D. The split CAT system facilitates the study of E3 ligases that cannot be purified from $E.\ coli$ such as UBE3B. Shown is UBE3B dependent ubiquitination of Rpn10 in the split CAT system. Kaufman syndrome mutation (G781R) in UBE3B shows a phenotype.

Figure 7:
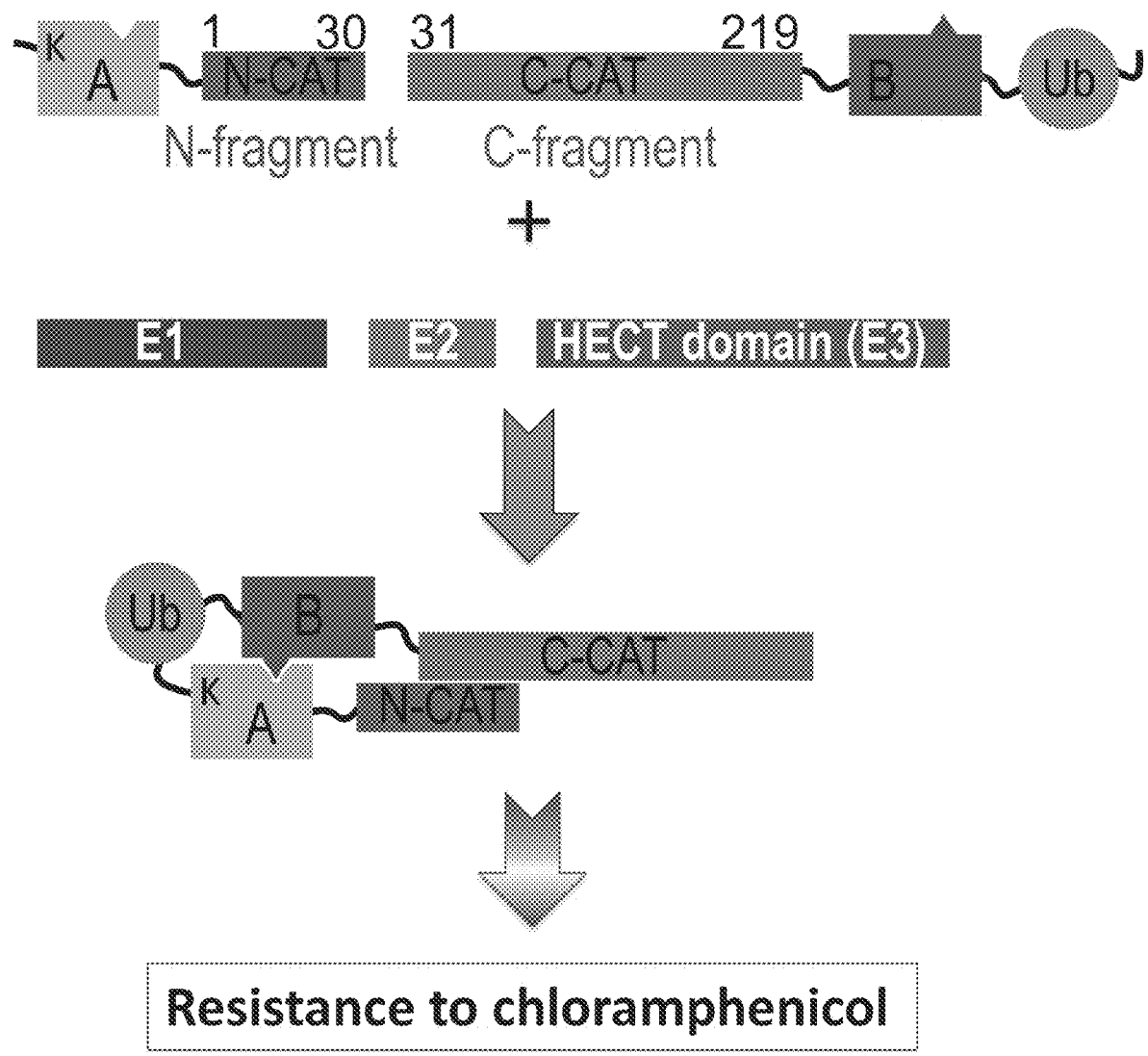

FIG. 7 is a diagram illustrating identification and characterization of ultra-weak PPIs. A scheme shows how the expression of ubiquitylation cascade can be employed to identify and characterize ultra-weak PPIs in bacteria.

FIGS. 8A-B Sequence of CAT. The DNA sequence and the translation products of $CAT_I$ is illustrated in FIG. 8A (SEQ ID NO: 1 for the protein and SEQ ID NO: 8 for the DNA sequence). Arrow marks the cleavage site that was chosen for the split protein fragments (A). The DNA sequence and the translation products of the split-$CAT_I$ fragments are shown in FIG. 8B. The N terminal protein sequence is as set forth in SEQ ID NO: 2. The N terminal DNA sequence is as set forth in SEQ ID NO: 4. The C terminal protein sequence is as set forth in SEQ ID NO: 3. The C terminal DNA sequence is as set forth in SEQ ID NO: 5. The stop codon after residue Q30 and the initiation codon prior residue C31 are shown in the split protein fragments (B).

FIG. 9 provides a list of CAT proteins that have a homology range of 79-100% identity to SEQ ID NO: 1. Arrows represent the conserved split site among all the family protein members. Accession codes are in blue. The sequence AFQSVAQCTYNQTVQLDI is set forth in SEQ ID NO: 11.

DESCRIPTION OF SPECIFIC EMBODIMENTS OF THE INVENTION

The present invention, in some embodiments thereof, relates to a chloramphenicol-resistant split protein and uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Split DHFR (dihydrofolate reductase) is a split antibiotic resistance protein that is based on resistance to the bacteriostatic antibiotic trimethoprim. DHFR is a key enzyme in the synthetic pathways of thymidine and several amino acids and therefore it becomes essential under conditions where one or few of these metabolites are missing or limited.

To ensure selective conditions using this split protein, the growth media must lack the restrictive metabolite (such as thymidine). In addition to the extended labor required in the preparation of the minimal media, its use significantly slows down the growth, making it difficult to quantify the growth rate/efficiency over a typical time period of 3-5 days. Moreover, with conventional bacteria seeding per plate (of ~$10^9$), the limitation of metabolite(s) in the media is compensated for as the degraded bacteria nourish the media with the missing metabolite(s).

To utilize a split resistance marker that resists a bacteriostatic antibiotic but is not based on the lack of metabolite(s), the present inventors invented a novel genetic selection tool based on split-CAT (Chloramphenicol Acetyl-Transferase) which resists the bacteriostatic antibiotic chloramphenicol. Chloramphenicol leads to bacterial growth arrest as it binds and inhibits the ribosome and therefore stops protein synthesis. Like other bacteriostatic antibiotics, washing out the chloramphenicol from the media that contains a naïve bacterial culture permits the growth of the arrested bacteria. Therefore, the predicted benefit of split-CAT over split-DHFR is the possibility to use a rich media for selection that enhances growth. It is predicted that such as marker will shorten experimental time and facilitate the quantification and analysis of the results.

Thus, according to a first aspect of the present invention there is provided a construct system comprising:

(i) a first nucleic acid construct comprising a first polynucleotide having a nucleic acid sequence that encodes an N-terminal fragment of chloramphenicol acetyl transferase (CAT), the N-terminal fragment comprising a first portion of the catalytic active site of the CAT, the N-terminal fragment being devoid of acetylating activity; and (ii) a second nucleic acid construct comprising a second polynucleotide having a nucleic acid sequence that encodes a C terminal fragment of the CAT, the C-terminal fragment comprising a second portion of the catalytic active site of the CAT, the C-terminal fragment being devoid of acetylating activity; and wherein the N-terminal fragment is capable of associating with the C-terminal fragment to generate an active CAT that is capable of acetylating chloramphenicol.

The construct system of the present invention is useful in detecting interaction between, for example, a known first member of a putative binding pair and a second member, for example one which was previously not known to bind the first member. The method detects the interaction of the first member with the second member by bringing into close proximity members of a fragment pair of the CAT reporter protein, such that the CAT reporter protein is reassembled to its original functionality or enzymatic activity. The fragments of the reporter protein of the present invention interact to bring about antibiotic resistance. This system enables, for example, the identification of molecules and/or genes that promote or inhibit key protein interactions, existing in a range of cell types, phyla and species, via high-throughput screens.

As used herein, the term CAT refers to an enzyme (EC 2.3.1.28) that catalyzes the acetyl-S-CoA-dependent acetylation of chloramphenicol at the 3-hydroxyl group.

In one embodiment, the CAT is $CAT_I$. In another embodiment, the CAT is $CAT_{II}$. In still another embodiment, the CAT is $CAT_{III}$.

The CAT of this embodiment may have an amino acid sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% homologous or identical to the sequence as set forth in SEQ ID NO: 1, as determined using the Standard protein-protein BLAST [blastp] software of the NCBI.

In one embodiment the CAT is an orthologue of CAT which comprises the amino acid sequence QC in its active site. Preferably the CAT orthologue comprises the sequence as set forth in SEQ ID NO: 11—such as those listed in FIG. 9.

In one embodiment the N-terminal fragment comprises a first portion of the catalytic active site of the CAT—e.g. the N terminal fragment typically contains the first 28 or 30 amino acids of the native CAT. The C-terminal fragment comprises the second portion of the catalytic active site of the CAT—for example, the C terminal fragment typically contains the rest of the sequence of the native CAT. The N-terminal fragment associates with the C-terminal fragment to generate an active CAT that is capable of acetylating chloramphenicol.

Preferably, the first amino acid of the C-terminal fragment is a small amino acid residue—for example cysteine or alanine. Thus, the C terminal fragment may begin with cysteine 31 (wherein the numbering is according to SEQ ID NO: 1), or alanine 29 (wherein the numbering is according to SEQ ID NO: 1). Other small amino acid residues include glycine, alanine, serine, proline, threonine, aspartate and asparagine.

By being small, the first amino acid of the C-terminal fragment after the formyl-methionine causes the latter to be post-translationally removed from the N-terminus (of the C-terminus fragment) hence salvaging the active site arrangement, as confirmed by the activity of the CAT.

In one embodiment, the N-terminal fragment comprises an amino acid sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% homologous or identical to the sequence as set forth in SEQ ID NO: 2 or 6. The N-terminal fragment may consist of the sequence as set forth in SEQ ID NO: 2 or SEQ ID NO: 6.

The C-terminal fragment comprises an amino acid sequence that is at least 70%, 71%, 72%, 73%, 74%, 75%, 76%, 77%, 78%, 79%, 80%, 81%, 82%, 83%, 84%, 85%, 86%, 87% , 88%, 89%, 90%, 91%, 92%, 93%, 94%, 95%, 96%, 97%, 98%, 99% or 100% homologous or identical to the sequence as set forth in SEQ ID NO: 3 or 7.

The C-terminal fragment may consist of the sequence as set forth in SEQ ID NO: 3 or 7.

According to a particular embodiment, the N-terminal fragment is encoded by the nucleic acid sequence as set forth in SEQ ID NO: 4.

The C-terminal fragment may be encoded by the nucleic acid sequence as set forth in SEQ ID NO: 5.

The DNA and protein sequence of an exemplary split CAT is illustrated in FIG. 8B.

Nucleic acid constructs includes a promoter sequence for directing transcription of the polynucleotide sequence in the cell in a constitutive or inducible manner.

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase; or synthetically synthesized by assembled from short oligonucleotide.

As used herein the phrase "genomic polynucleotide sequence" refers to a sequence derived (isolated) from a chromosome and thus it represents a contiguous portion of a chromosome. As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, a typical cloning vector may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

Exemplary promoters contemplated by the present invention include, but are not limited to polyoma, Simian Virus 40 (SV40), adenovirus, retroviruses, hepatitis-B virus and cytomegalovirus promoters. According to a particular embodiment, the promoter is a bacterial promoter.

Constitutive promoters suitable for use with the present invention are promoter sequences which are active under most environmental conditions and most types of bacterial cells such as an unregulated bacteriophage lambda left promoter (pL) or pTac which presents high leakiness.

Enhancer elements can stimulate transcription up to 1,000 fold from linked homologous or heterologous promoters. Enhancers are active when placed downstream or upstream from the transcription initiation site. Many enhancing elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

In a preferred embodiment, the vector comprises a bacterial replication of origin.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

The use of bacterial operon architecture for multi-gene expression, where a single promoter is followed by several open reading frames (ORFs) each contains a ribosome-binding site (Shine-Dalgarno sequence) facilitates the co-expression of the multi-protein complex of the ubiquitination apparatus.

It will be appreciated that the individual elements comprised in the expression vector can be arranged in a variety of configurations. For example, enhancer elements, promoters and the like, and even the polynucleotide sequence(s) encoding the fusion protein can be arranged in a "head-to-tail" configuration, may be present as an inverted complement, or in a complementary configuration, as an antiparallel strand. While such variety of configuration is more likely to occur with non-coding elements of the expression vector, alternative configurations of the coding sequence within the expression vector are also envisioned.

Other than containing the necessary elements for the transcription and translation of the inserted coding sequence, the expression construct of some embodiments of the invention can also include sequences engineered to enhance stability, production or isolation of the expressed peptide fragments.

Preferably, the N and C terminal fragments are devoid of signal sequences which allow for them to be secreted from the bacterial cells. Thus, the N and C terminal fragments are expressed in the cytoplasm of the bacterial cells and are not secreted.

Examples of bacterial constructs include the pET series of E. Coli expression vectors (see for example Studier et al (1990) Methods in Enzymol 185:60-89) in which their T7 promoter was replaced with the constitutive active bacteriophage pH (left promoter). Other vectors that may be used are those that belong to the pZE vector family (e.g. pZE21), those that belong to the pCloDF (containing a pCloDF13 origin) and pACYC (containing a p15A origin of replication).

Exemplary methods of introducing the polynucleotides of the present invention into prokaryotic cells are well known in the art—these include, but are not limited to, transforming with a recombinant bacteriophage DNA, plasmid DNA or cosmid DNA expression vector containing the relevant gene sequences.

The first and/or second polynucleotide of this aspect of the present invention may further comprise a cloning site. The position of the cloning site is selected such that upon insertion of a sequence which encodes a test polypeptide into the cloning site, following expression in a cell, a fusion protein is generated which comprises the test polypeptide in frame with the C-terminal fragment.

As used herein, the term "cloning site" refers to a nucleic acid sequence containing a restriction site for restriction endonuclease-mediated cloning by ligation of a nucleic acid containing compatible cohesive or blunt ends.

Alternatively, the polynucleotides described herein may comprise a region of nucleic acid serving as a priming site for PCR-mediated cloning of insert DNA by homology and extension "overlap PCR stitching," or a recombination site for recombinase-mediated insertion of target nucleic acids by recombination-exchange reaction, or mosaic ends for transposon mediated insertion of target nucleic acids, as well as other techniques common in the art.

The first nucleic acid construct of the system described herein may further comprise a nucleic acid sequence that encodes a first test polypeptide at a position such that, following expression in a cell, a fusion protein is generated which comprises the test polypeptide in frame with the N-terminal fragment.

The second construct of the system described herein may further comprise a nucleic acid sequence that encodes a second test polypeptide at a position such that, following expression in a cell, a fusion protein is generated which comprises the test polypeptide in frame with the C-terminal fragment. The first and second test polypeptide are optionally members of a putative binding pair.

Binding of the test polypeptides of the present invention to one another will depend upon factors such as pH, ionic strength, concentration of components of the assay, and temperature. In the binding assays using the reporter systems described herein, the binding affinity of the first member of the putative binding pair and the second member of the putative binding pair should be strong enough to permit binding between the reporter protein fragments. In a preferred embodiment, the binding affinity of the first member of the putative binding pair and the second member of the putative binding pair should be stronger than the binding affinity of the first fragment and the second fragment of the reporter protein. When combining the first and second fusion proteins, the reconstitution of the first and second fragments into the reporter protein requires the interaction between the first and second members of the putative binding pair.

The members of a putative binding pair which can be assayed for their binding affinity with each other, using the methods of the present invention, include any molecules capable of a binding interaction. The binding interaction between the two or more binding members may be either direct or in the form of a complex with one or more additional binding species, such as charged ions or molecules, ligands, or macromolecules. Putative binding partners, or putative binding moieties, according to the present invention, can include molecules which do not normally interact with each other, but which interact with a third molecule such that, in the presence of the third molecule, the putative binding partners are brought together. Thus, substances which influence an interaction between putative binding partners include those which stimulate a weak interaction between putative binding partners, as well as one or more molecules which mediate interaction between molecules which do not normally interact with each other. In addition, substances which influence an interaction between putative binding partners can include those which directly or indirectly affect an upstream event which results in association between the putative binding partners. For example, phosphorylation of one of the putative binding partners can endow it with the capacity to associate with another of the putative binding partners.

Exemplary putative binding pairs include membrane protein-soluble binding protein pair, a membrane protein-membrane protein binding pair, a biotin-avidin binding pair, ligand-receptor binding pair, and antibody-antigen binding pair.

In an antigen-antibody pair, for example, the antibody can be a monoclonal antibody, bispecific antibody, single-chain antibody (scAb), single-chain Fv fragment (scFv), $scFv_2$, dsFv, scFv-Fc, Fab, $F(ab')_2$, $F(ab)_3$, $V_L$, diabody, single domain antibody, camelid antibody, triabody, tetrabody, minibody, one-armed antibody, and immunoglobulins (Igs) including, but not limited to IgM, IgE, IgA, IgD or IgG.

The ligand-receptor pairs of the present invention can include, for example, the following receptors Fc receptors (FcR), single-chain MHC, or single-chain T-cell receptor (sc-TCR). Useful ligands are, for example, monotopic membrane proteins, polytopic membrane proteins, transmembrane proteins, G protein-coupled receptors (GPCRs), ion channels, members of the SNARE protein family, integrin adhesion receptor, multi-drug efflux transporters.

Other exemplary proteins include members of the signal transduction pathway, cell surface receptors, proteins regulating apoptosis, proteins that regulate progression of the cell-cycle, proteins involved in the development of tumors, transcriptional-regulatory proteins, translation regulatory proteins, proteins that affect cell interactions, cell adhesion molecules, proteins that participate in the folding of other proteins, and proteins involved in targeting to intracellular compartments.

Members of signal transduction pathways include protein hormones and cytokines Cytokines include those involved in signal transduction, such as interferons, chemokines, and hematopoietic growth factors. Other exemplary proteins include interleukins, lymphotoxin, transforming growth factors-a and 13, and macrophage and granulocyte colony stimulating factors. Other proteins include intracellular enzymes such as protein kinases, phosphatases and synthases.

Exemplary proteins involved in apoptosis include tumor necrosis factor (TNF), Fos ligand, interleukin-113 converting enzyme (ICE) proteases, and TNF-related apoptosis-inducing ligand (TRAIL). Proteins involved in the cell cycle include deoxyribonucleic acid (DNA) polymerases, proliferating cell nuclear antigen, telomerase, cyclins, cyclin dependent kinases, tumor suppressors and phosphatases. Proteins involved in transcription and translation include ribonucleic acid (RNA) polymerases, transcription factors, enhancer-binding proteins and ribosomal proteins. Proteins involved in cellular interactions such as cell-to-cell signaling include receptor proteins, and peptide hormones or their enhancing or inhibitory mimics.

In one embodiment, either one or both the first and second members of the putative binding pair can be a member of a library. The members of the putative binding pair can be parts of libraries that are constructed from cDNA, but may also be constructed from, for example, synthetic DNA, RNA and genomic DNA.

In one embodiment, the constructs are used to study ubiquitination.

In one embodiment, the N terminus of the N-terminal fragment is linked to the C terminus of the ubiquitin substrate or ubiquitin (preferably via a linker).

In another embodiment, the C terminus of the C-terminal fragment is linked to the N terminus of the ubiquitin substrate or ubiquitin (preferably via a linker, as further described herein below).

The term "ubiquitin" as used herein refers to either mammalian ubiquitin having a sequence MQIFVKTLTGK-TITLEVEPSDTIENVKAKIQDKEGIPPDQQ RLIF-AGKQLEDGRTLSDYNIQKESTLHLVLRLRGG (SEQ ID NO: 9) or yeast ubiquitin having a sequence MQIFVKTLTGKTITLEVESSDTIDNVKSKIQDKEG-IPPDQQRLIFAGKQLEDGR LSDY-NIQKESTLHLVLRLRGG (SEQ ID NO: 10).

Examples of ubiquitin substrates include polypeptides that are known to be ubiquitinated in vivo in humans by E3 ligase or deubiquitinated in vivo by deubiquitinating enzymes.

According to a specific embodiment, the substrate is one that is known to be ubiquitinated differentially in a disease such as cancer.

According to a particular embodiment, the substrate is selected from the group consisting of PHD3, SPROUTY2, Mitofusin 1, 2, MIRO, NEMO, SMADs, TβR-I, P53, S5A, HHR23, EPHEXIN5, ARC, PPARα, cyclin-B, Cdc25C and Calmodulin.

Additional substrates are described herein below.

Since ubiquitination takes place by a cascade of enzyme activity (i.e. a plurality of enzymes which work together to bring about the same function—ubiquitination), the present invention further contemplates expressing ubiquitinating enzymes. Thus nucleic acid constructs for the expression of such enzymes may also be part of the construct system described herein.

In one embodiment, the construct includes a construct for the expression of at least one E1 enzyme, at least one E2 enzyme and at least one E3 enzyme.

Preferably, the construct system includes a construct for expression of an E2 enzyme that is a cognate pair for the E3 enzyme.

In another embodiment, the system includes a construct for expression of at least one deubiquitinating enzyme.

In one system, the E1 and E2 enzyme are expressed from the same construct as the ubiquitin and the E3 enzyme is expressed from the same construct as the substrate.

In another embodiment, the E1 and E2 enzyme are expressed from the same construct as the substrate and the E3 enzyme is expressed from the same construct as the ubiquitin.

In still a further embodiment, the E1 and E2 enzyme are expressed from the same construct as the substrate and/or the ubiquitin and the E3 enzyme is expressed from an additional expression construct.

The additional expression construct from which the E3-ligase is expressed may use a different selection marker as that used for the other constructs (e.g. Amp$^R$ selection marker). It may also use a different origin of replication such as p15A. The promoter for this expression construct may be inducible or constitutive. In one embodiment, the promoter is a weak constitutive promoter such as the pTac promoter which is leaky without the addition of inducer (IPTG).

As used herein, the term "ubiquitinating enzyme" refers to ubiquitin-activating enzymes (E1s), ubiquitin-conjugating enzymes (E2s) or ubiquitin ligases (E3s). Collectively they have the EC number EC 6.3.2.19.

In one embodiment, the ubiquitinating enzyme is a human ubiquitinating enzyme.

Ubiquitin-activating enzymes (E1s) have the EC number EC 6.2.1.45, ubiquitin-conjugating enzymes have the EC number EC 2.3.2.23 and ubiquitin ligases have the EC number 2.3.2.27.

Table 1, herein below provides nomenclature and most common synonyms used for E2 ubiquitin conjugating enzymes. The E2 nomenclature is in accordance with that used by the Human Genome Organization.

TABLE 1

| Human Genome Organization Nomenclature | Synonym |
|---|---|
| UBE2V2 | UEV2/MMS2 |
| UBE2D1 | UBC4/5/UBCH5A |
| UBE2D2 | UBC4/5/UBCH5B |
| UBE2D4 | HBUCE1 |
| UBE2D3 | UBC4/5 |
| UBE2W | FLJ11011 |
| UBE2B | UBC2/HHR6B/RAD6B/E217K |
| UBE2L6 | RIGB/UBCH8 |
| UBE2N | UBC13 |
| UBE2L3 | UBCH7 |
| UBE2G1 | UBC7/E217K |
| UBE2H | UBC8/E220K |
| UBE2M | UBC12 |
| UBE2F | NCE2 |
| UBE2E2 | UBCH8 |
| UBE2E3 | UBCH9/UBCM2 |
| UBE2S | E224K |
| UBE2U | MGC35130 |
| UBE2R1 | CDC34 |
| UBE2R2 | UBC3B/CDC34B |
| UBE2Z | HOYS7 |
| UBE2J2 | NCUBE2 |
| Probable ubiquitin-conjugating enzyme E2 FLJ25076 | LOC134111/FLJ25076 |
| AKTIP | FTS/FT1 |
| UBE2J1 | NCUBE1 |
| UBE2V1 | UEV1/CROC1 |
| UBE2Q2 | DKFZ/UBCI |
| UBE2Q1 | NICE5 |
|  | TSG101/VPS23/SG10 |
| UEVLD | UEV3 |

In one embodiment, the ubiquitinating enzyme is an E3 ligase.

Exemplary E3 ligases contemplated by the present invention include, but are not limited to Siah2, Smurf1, MDM2, BRCA1, PARKIN, UBE3A, TRIM5, NEDD4, UBR5, bTrCP, CRBN, FbxW7, Huwe1, Arkadia, ITCH, MuRF1, TRAF6, Trim32, UBR4, UBE3B and UBE3D.

According to a particular embodiment, the E3 ligase is selected from the group consisting of Siah2, Smurf1, MDM2, BRCA1, PARKIN, UBE3A, UBE3B, MURF1, TRIM32, TRIM5, NEDD4, UBR5 and Huwe1.

In another embodiment the E3 ligase is Siah2, Smurf1, MDM2, BRCA1, PARKIN or UBE3A.

Below is a brief description of exemplary E3 ligases contemplated by the present invention and some of their exemplary substrates.

Seven in Absentia Homolog 2 (SIAH2)

SIAH2 is a RING finger type ubiquitin ligases with a catalytic RING domain on its N-terminus, followed by two zinc fingers and a C-terminal substrate binding domain.

Siah2 is an E3 ubiquitin ligase implicated in diverse biological processes including p38/JNK/NF-kB signaling pathways, DNA damage, estrogen signaling, programmed cell death, Ras/Raf pathway, mitosis, and hypoxia.

Siah2 targets numerous substrates for degradation including TRAF2 (ketoglutarate dehydrogenase), Spry2 (Sprouty2), and the prolyl hydroxylase PHD3.

Siah2 also limits its own availability through self-ubiquitination and degradation.

Siah2 play a key role in hypoxia, through the regulation of HIF-1α transcription stability and activity via regulation of PHD3 stability.

Smad Ubiquitination Regulatory Factor-1 (Smurf1)

Smurf1 is a NEDD4-like Class IV HECT (homologous to E6-AP carboxylterminus) family E3 ligase with catalytic activity.

Smurf1 has been linked to several important biological pathways, including the bone morphogenetic protein pathway, the non-canonical Wnt pathway, and the mitogen-activated protein kinase pathway.

Smurfs possess three functional domains: an N-terminal protein kinase C (PKC)-related C2 domain which binds to phospholipids, targeting Smurfs to intracellular membranes, a central region containing two to four WW (tryptophan residues) protein-interacting domains which mediate ligase-substrate associations through interactions with a variety of proline-rich (PPXY) motifs and proline-containing phosphoserine/phosphothreonine sequences of the protein substrate, and a C-terminal HECT domain, responsible for ubiquitin transfer from a conserved cysteine residue at position 716 to a lysine residue in a substrate protein.

Smurf1 promotes p53 degradation by enhancing the activity of the E3 ligase MDM2. Smurf1 stabilizes MDM2 by enhancing the heterodimerization of MDM2 with MDMX, during which Smurf1 interacts with MDM2 and MDMX.

Smurf1 is also a key negative regulator of transforming growth factor (TGF)-β/bone morphogenetic protein (BMP) signaling pathway.

Mouse Double Minute 2 Homolog (MDM2)

MDM2 also known as E3 ubiquitin-protein ligase Mdm2 is an important negative regulator of the p53 tumor suppressor.

Mdm2 protein functions both as an E3 ubiquitin ligase that recognizes the N-terminal trans-activation domain (TAD) of the p53 tumor suppressor and as an inhibitor of p53 transcriptional activation.

Mdm2 contains a C-terminal RING domain (amino acid residues 430-480), which contains a Cis3-His2-Cis3 consensus that coordinates two molecules of zinc. These residues are required for zinc binding, which is essential for proper folding of the RING domain. The RING domain of Mdm2 confers E3 ubiquitin ligase activity and is sufficient for E3 ligase activity in Mdm2 RING autoubiquitination. The RING domain of Mdm2 is unique in that it incorporates a conserved Walker A or P-loop motif characteristic of nucleotide binding proteins, as well as a nucleolar localization sequence.

Mdm2 is capable of auto-polyubiquitination, and in complex with p300, a cooperating E3 ubiquitin ligase, is capable of polyubiquitinating p53. In this manner, Mdm2 and p53 are the members of a negative feedback control loop that keeps the level of p53 low in the absence of p53-stabilizing signals.

BRCA1

BRCA1-BARD1 constitutes a heterodimeric RING finger complex of the BRCA1/BRCA2-containing complex (BRCC) that contains significant ubiquitin ligase activity.

BRCA1 plays critical roles in the repair of chromosomal damage (error-free repair of DNA double-strand breaks), cell cycle checkpoint control, and genomic stability.

BRCA1 forms several distinct complexes through association with different adaptor proteins, and each complex forms in a mutually exclusive manner.

BRCA1 combines with other tumor suppressors, DNA damage sensors and signal transducers to form a large multi-subunit protein complex known as the BRCA1-associated genome surveillance complex (BASC).

The BRCA1 protein associates with RNA polymerase II, and through the C-terminal domain, also interacts with histone deacetylase complexes. Thus, this protein plays a role in transcription, DNA repair of double-strand breaks ubiquitination, transcriptional regulation as well as other functions.

Parkin

Parkin is a RING-between-RING E3 ligase that functions in the covalent attachment of ubiquitin to specific substrates.

It is best known for regulating the disposal of dysfunctional mitochondria (together with PINK1, a serine threonine kinase) via mitochondrial autophagy (i.e., mitophagy).

Upon loss of mitochondrial membrane potential, PINK1 becomes stabilized and activated on the outer mitochondrial membrane (OMM), resulting in recruitment and activation of Parkin.

Parkin facilitates ubiquitination of a broad number of targets expressed on the OMM (e.g., TOM20, Mitofusins, VDAC, Fis1) resulting in recruitment of the autophagy machinery, autophagosome formation and mitochondrial clearance.

In addition to its established role in mitophagy and UPS, Parkin impacts other neuroprotective cellular pathways, including TNFα signaling, and Wnt/β catenin signaling, and is also a putative tumor suppressor.

UBE3A (Gene Coding for E6-Associated Protein; E6-AP)

This ligase promotes the ubiquitylation and degradation of p53. E6-AP was subsequently shown to ubiquitylate proteins independent of E6 and to serve an independent secondary function as a transcriptional co-activator of nuclear estrogen receptors. E6-AP has been implicated in a broad range of processes (e.g. cell growth, synaptic formation and function, etc.) and has been shown to have many different target substrates (e.g., HHR23A, CDKN1B, MCM7, etc.).

Tripartite Motif-5 (TRIM5)

This ligase is a RING finger E3 ligase a key anti-viral restriction factor and directly involved in inhibiting HIV-1 replication.

Neural Precursor Cell Expressed Developmentally Downregulated 4 (NEDD4-1)

Nedd4-1 ubiquitinates a number of substrates, including ENaC, FGFR1, ADRB2, AMPA, Notch, pAKT, VEGFR2, EPS15, LATS1, and MDM2.

The vacuolar protein sorting protein Alix recruits NEDD4 to HIV-1 Gag protein to facilitate HIV-1 release via a mechanism that involves Alix ubiquitination.

NEDD4 also binds and ubiquitinates the latent membrane protein 2A (LMP2A) of the Epstein-Bar virus (EBV) to activate B-cell signal transduction.

Ubiquitin Protein Ligase E3 Component N-Recognin 5 (UBR5)

This ligase is also known as EDD (E3 identified by Differential Display), EDD1, HHYD, KIAA0896, or DD5.

URB5 acts as a general tumor suppressor by ubiquitinating, which increases p53 levels and induces cell senescence. UBR5 also ubiquitinates TopBP1, a topo-isomerase that intervenes in DNA damage response.

HUWE1

HUWE1 (also known as ARF-BP1, MULE, LASU1, or HECTH9) is an E3 ligase that regulates the stability of diverse cellular substrates and, in consequence, numerous physiological processes, including DNA replication and damage repair, cell proliferation and differentiation, and apoptosis.

HUWE1 substrates include both tumor promoters (e.g., N-MYC, C-MYC, MCL1) and suppressors (e.g., p53, MYC, MIZ1).

HUWE1 has demonstrated both pro-oncogenic and tumor-suppressor functions in different tumor models.

HUWE1 belongs to the HECT (Homologous to E6AP C-Terminus)-family of ubiquitin E3 ligases.

Other additional E3 ligases and their substrates are provided in Table 2, herein below.

TABLE 2

| Ligase | Substrate | Function |
| --- | --- | --- |
| AMFR | KAI1 | AMFR is also known as gp78. AMFR is an integral ER membrane protein and functions in ER-associated degradation (ERAD). AMFR has been found to promote tumor metastasis through ubiquitination of the metastasis supressor, KAI1. |
| APC/Cdc20 | Cyclin B | The anaphase promoting complex/cyclosome (APC/C) is a multiprotein complex with E3 ligase |

TABLE 2-continued

| Ligase | Substrate | Function |
|---|---|---|
| | | activity that regulates cell cycle progression through degradation of cyclins and other mitotic proteins. APC is found in a complex with CDC20, CDC27, SPATC1, and TUBG1. |
| APC/Cdh1 | Cdc20, Cyclin B, Cyclin A, Aurora A, Securin, Skp2, Claspin | The anaphase promoting complex/cyclosome (APC/C) is a multiprotein complex with E3 ligase activity that regulates cell cycle progression through degradation of cyclins and other mitotic proteins. The APC/C-Cdh1 dimeric complex is activated during anaphase and telophase, and remains active until onset of the next S phase. |
| C6orf157 | Cyclin B | C6orf157 is also known as H10BH. C6orf157 is an E3 ubiquitin ligase that has been shown to ubiquitinate cyclin B. |
| Cbl | | Cbl-b and c-Cbl are members of the Cbl family of adaptor proteins that are highly expressed in hematopoietic cells. Cbl proteins possess E3 ubiquitin ligase activity that downregulates numerous signaling proteins and RTKs in several pathways such as EGFR, T cell and B cell receptors, and integrin receptors. Cbl proteins play an important role in T cell receptor signaling pathways. |
| CBLL1 | CDH1 | CBLL1 is also known as Hakai. CBLL1 is an E3 ubiquitin ligase that ubiquitinates the phosphorylated form of E-Cadherin, causing its degradation and loss of cell-cell adhesions. |
| CHFR | PLK1, Aurora A | CHFR is an E3 ubiquitin ligase that functions as a mitotic stress checkpoint protein that delays entry into mitosis in response to stress. CHFR has been shown to ubiquitinate and degrade the kinases PLK1 and Aurora A. |
| CHIP | HSP70/90, iNOS, Runx1, LRRK2 | CHIP is an E3 ubiquitin ligase that acts as a co-chaperone protein and interacts with several heat shock proteins, including HSP70 and HSP90, as well as the non-heat shock proteins iNOS, Runx1 and LRRK2. |
| DTL (Cdt2) | p21 | DTL is an E3 ubiquitin ligase that complexes with Cullin4 and DDB1, and promotes p21 degradation after UV damage. |
| E6-AP | p53, Dlg | E6-AP is also known as UBE3A. E6-AP is a HECT domain E3 ubiquitin ligase that interacts with Hepatitis C virus (HCV) core protein and targets it for degradation. The HCV core protein is central to packaging viral DNA and other cellular processes. E6-AP also interacts with the E6 protein of the human papillomavirus types 16 and 18, and targets the p53 tumor-suppressor protein for degradation. Mutations that decrease UBE3A activity may cause Angelman syndrome. Mutations that increase UBE3A activity may cause Autism syndrome. |
| HACE1 | | HACE1 is an E3 ubiquitin ligase and tumor suppressor. Aberrant methylation of HACE1 is frequently found in Wilms' tumors and colorectal cancer. |
| HECTD1 | | HECTD1 is an ubiquitin E3 ligase required for neural tube closure and normal development of the mesenchyme. |
| HECTD2 | | HECTD2 is a probable E3 ubiquitin ligase and may act as a susceptibility gene for neurodegeneration and prion disease. |
| HECTD3 | | HECTD3 is a probable E3 ubiquitin ligase and may play a role in cytoskeletal regulation, actin remodeling, and vesicle trafficking. |
| HECW1 | DVL1, mutant SOD1, p53 | HECW1 is also known as NEDL1. HECW1 interacts with p53 and the Wnt signaling protein DVL1, and may play a role in p53-mediated cell death in neurons. |
| HECW2 | p73 | HECW2 is also known as NEDL2. HECW2 ubiquitinates p73, which is a p53 family member. Ubiquitination of p73 increases protein stability. |
| HERC2 | RNF8 | HERC2 belongs to a family of E3 ubiquitin ligases involved in membrane trafficking events. HERC2 plays a role in the DNA damage response through interaction with RNF8. |
| HERC3 | | HERC3 belongs to a family of E3 ubiquitin ligases involved in membrane trafficking events. HERC3 interacts with hPLIC-1 and hPLIC-2 and localizes to the late endosomes and lysosomes. |
| HERC4 | | HERC4 belongs to a family of E3 ubiquitin ligases involved in membrane trafficking events. HERC4 is highly expressed in testis and may play a role in spermatogenesis. |
| HERC5 | | HERC5 belongs to a family of E3 ubiquitin ligases involved in membrane trafficking events. HERC5 is induced by interferon and other pro-inflammatory cytokines and plays a role in interferon-induced ISG15 conjugation during the innate immune response. |
| HUWE1 | N-Myc, C-Myc, p53, Mcl-1, TopBP1 | HUWE1 is also known as Mule. HUWE1 is a HECT domain E3 ubiquitin ligase that regulates degradation of Mcl-1 and therefore regulates DNA damage-induced apoptosis. HUWE1 also controls neuronal differentiation by destabilizing N-Myc, and regulates p53-dependent and independent tumor suppression via ARF. |
| HYD | CHK2 | HYD is also known as EDD or UBR5. HYD is a regulator of the DNA damage response and is overexpressed in many forms of cancer. |
| ITCH | MKK4, RIP2, Foxp3 | ITCH plays a role in T cell receptor activation and signaling through ubiquitination of multiple proteins including MKK4, RIP2 and Foxp3. Loss of ITCH function leads to an aberrant immune response and T helper cell differentiation. |
| LNX1 | NUMB | LNX1 is an E3 ubiquitin ligase that plays a role in cell fate determination during embryogenesis through regulation of NUMB, the negative regulator of Notch signaling. |
| mahogunin | | Mahogunin is an E3 ubiquitin ligase involved in melanocortin signaling. Loss of mahogunin function leads to neurodegeneration and loss of pigmentation, and may be the mechanism of action in prion disease. |

TABLE 2-continued

| Ligase | Substrate | Function |
|---|---|---|
| MARCH-I | HLA-DRβ | MARCH1 is an E3 ubiquitin ligase found on antigen presenting cells (APCs). MARCH1 ubiquitinates MHC class II proteins and downregulates their cell surface expression. |
| MARCH-II | | MARCH-II is a member of the MARCH family of E3 ubiquitin ligases. It associates with syntaxin6 in the endosomes and helps to regulate vesicle trafficking. |
| MARCH-III | | MARCH-III is a member of the MARCH family of E3 ubiquitin ligases. MARCH-III associates with syntaxin6 in the endosomes and helps to regulate vesicle trafficking. |
| MARCH-IV | MHC class I | MARCH-IV is a member of the MARCH family of E3 ubiquitin ligases. MARCH-IV ubiquitinates MHC class I proteins and downregulates their cell surface expression. |
| MARCH-VI | | MARCH-VI is also known as TEB4 and is a member of the MARCH family of E3 ubiquitin ligases. It localizes to the endoplasmic reticulum and participates in ER-associated protein degradation. |
| MARCH-VII | gp190 | MARCH-VII is also known as axotrophin. MARCH-VII was originally identified as a neural stem cell gene, but has since been shown to play a role in LIF signaling in T lymphocytes through degradation of the LIF-receptor subunit, gp190. |
| MARCH-VIII | B7-2, MHC class II | MARCH-VIII is also known as c-MIR. MARCH-VIII causes the ubiquitination/degradation of B7-2, which is a co-stimulatory molecule for antigen presentation. MARCH-VIII has also been shown to ubiquitinate MHC class II proteins. |
| MARCH-X | | MARCH-X is also known as RNF190. MARCH-X is a member of the MARCH family of E3 ubiquitin ligases. The putative role of MARCH-X is not currently known. |
| MDM2 | p53 | MDM2, an E3 ubiquitin ligase for p53, plays a central role in regulation of the stability of p53. Akt-mediated phosphorylation of MDM2 at Ser166 and Ser186 increases its interaction with p300, allowing MDM2-mediated ubiquitination and degradation of p53. |
| MEKK1 | c-Jun, Erk | MEKK1 is a well known protein kinase of the STE11 family. MEKK1 phosphorylates and activates MKK4/7, which in turn activates JNK1/2/3. MEKK1 contains a RING finger domain and exhibits E3 ubiquitin ligase activity toward c-Jun and Erk. |
| MIB1 | Delta, Jagged | Mindbomb homolog 1 (MIB1) is an E3 ligase that facilitates the ubiquitination and subsequent endocytosis of the Notch ligands, Delta and Jagged. |
| MIB2 | Delta, Jagged | Mind Bomb 2 (MIB2) is an E3 ligase that positively regulates Notch Signaling. MIB2 has been shown to play a role in myotube differentiation and muscle stability. MIB2 ubiquitinates NMDAR subunits to help regulate synaptic plasticity in neurons. |
| MycBP2 | Fbxo45, TSC2 | MycBP2 is an E3 ubiquitin ligase also known as PAM. MycBP2 associates with Fbxo45 to play a role in neuronal development. MycBP2 also regulates the mTOR pathway through ubiquitination of TSC2. |
| NEDD4 | | NEDD4 is an E3 ubiquitin ligase highly expressed in the early mouse embryonic central nervous system. NEDD4 downregulates both neuronal voltage-gated Na+ channels (NaVs) and epithelial Na+ channels (ENaCs) in response to increased intracellular Na+ concentrations. |
| NEDD4L | Smad2 | NEDD4L is an E3 ubiquitin ligase highly expressed in the early mouse embryonic central nervous system. NEDD4L has been shown to negatively regulate TGF-β signaling by targeting Smad2 for degradation. |
| Parkin | | Parkin is an E3 ubiquitin ligase that has been shown to be a key regulator of the autophagy pathway. Mutations in Parkin can lead to Parkinson's Disease. |
| PELI1 | TRIP, IRAK | PELI1 is an E3 ubiquitin ligase that plays a role in Toll-like Receptor (TLR3 and TLR4) signaling to NF-κB via the TRIP adaptor protein. PELI1 has also been shown to ubiquitinate IRAK. |
| Pirh2 | TP53 | Pirh2 is also known as RCHY1. Pirh2 is a RING domain E3 ubiquitin ligase. Pirh2 binds p53 and promotes proteosomal degradation of p53 independent of MDM2. Pirh2 gene expression is controlled by p53, making this interaction part of an autoinhibitory feedback loop. |
| PJA1 | ELF | PJA1 is also known as PRAJA. PJA1 plays a role in downregulating TGF-β signaling in gastric cancer via ubiquitination of the SMAD4 adaptor protein ELF. |
| PJA2 | | PJA2 is an E3 ubiquitin ligase found in neuronal synapses. The exact role and substrates of PJA2 are unclear. |
| RFFL | p53 | RFFL is also known as CARP2 and is an E3 ubiquitin ligase that inhibits endosome recycling. RFFL also degrades p53 through stabilization of MDM2. |
| RFWD2 | MTA1, p53, FoxO1 | RFWD2 is also known as COP1. RFWD2 is an E3 ubiquitin ligase that ubiquitinates several proteins involved in the DNA damage response and apoptosis including MTA1, p53, and FoxO1. |
| Rictor | SGK1 | Rictor interacts with Cullin1-Rbx1 to form an E3 ubiquitin ligase complex, and promotes ubiquitination and degradation of SGK1. |
| RNF5 | JAMP, paxillin | RNF5 is also known as RMA5. RNF5 plays a role in ER-associated degradation of misfolded proteins and ER stress response through ubiquitination of JAMP. RNF5 also plays a role in cell motility and has been shown to ubiquitinate paxillin. |
| RNF8 | H2A, H2AX | RNF8 is a RING domain E3 ubiquitin ligase that plays a role in the repair of damaged chromosomes. RNF8 ubiquitinates Histone H2A and H2A.X at double-strand breaks (DSBs) which recruits 53BP1 and BRCA1 repair proteins. |

TABLE 2-continued

| Ligase | Substrate | Function |
|---|---|---|
| RNF19 | SOD1 | RNF19 is also known as Dorfin. Accumulation and aggregation of mutant SOD1 leads to ALS disease. RNF19 ubiquitinates mutant SOD1 protein, causing a decrease in neurotoxicity. |
| RNF190 | | see MARCH-X |
| RNF20 | Histone H2B | RNF20 is also known as BRE1. RNF20 is an E3 ubiquitin ligase that monoubiquitinates Histone H2B. H2B ubiquitination is associated with areas of active transcription. |
| RNF34 | Caspase-8, -10 | RNF34 is also known as RFI. RNF34 inhibits death receptor mediated apoptosis through ubiquitination/degradation of caspase-8 and -10. |
| RNF40 | Histone H2B | RNF40 is also known as BRE1-B. RNF40 forms a protein complex with RNF20 resulting in the ubiquitination of Histone H2B. H2B ubiquitination is associated with areas of active transcription. |
| RNF125 | | RNF125 is also known as TRAC-1. RNF125 has been shown to positively regulate T cell activation. |
| RNF128 | | RNF128 is also known as GRAIL. RNF128 promotes T cell anergy and may play a role in actin cytoskeletal organization in T cell/APC interactions. |
| RNF138 | TCF/LEF | RNF138 is also known as NARF. RNF138 is associated with Nemo-like Kinase (NLK) and suppresses Wnt/β-Catenin signaling through ubiquitination/degradation of TCF/LEF. |
| RNF168 | H2A, H2A.X | RNF168 is an E3 ubiquitin ligase that helps protect genome integrity by working together with RNF8 to ubiquitinate Histone H2A and H2A.X at DNA double-strand breaks (DSB). |
| SCF/β-TrCP | IκBα, Wee1, Cdc25A, β-Catenin | SCF/β-TrCP is an E3 ubiquitin ligase complex composed of SCF (SKP1-CUL1-F-box protein) and the substrate recognition component, β-TrCP (also known as BTRC). SCF/β-TrCP mediates the ubiquitination of proteins involved in cell cycle progression, signal transduction, and transcription. SCF/β-TrCP also regulates the stability of β-catenin and participates in Wnt signaling. |
| SCF/FBW7 | Cyclin E, c-Myc, c-Jun | SCF/FBW7 is an E3 ubiquitin ligase complex composed of SCF (SKP1-CUL1-F-box protein) and the substrate recognition component, FBW7. SCF/FBW7 mediates the ubiquitination of proteins involved in cell cycle progression, signal transduction, and transcription. Target proteins for SCF/FBW7 include the phosphorylated forms of c-Myc, Cyclin E, Notch intracellular domain (NICD), and c-Jun. Defects in FBXW7 may be a cause of breast cancer. |
| SCF/Skp2 | p27, p21, Fox01 | SCF/Skp2 is an E3 ubiquitin ligase complex composed of SCF (SKP1-CUL1-F-box protein) and the substrate recognition component, Skp2. SCF/Skp2 mediates the ubiquitination of proteins involved in cell cycle progression (specifically the G1/S transition), signal transduction and transcription. Target proteins for SCF/Skp2 include the phosphorylated forms of p27Kip1, p21Waf1/Cip1, and FoxO1. |
| SHPRH | PCNA | SHPRH is an E3 ubiquitin ligase that plays a role in DNA replication through ubiquitination of PCNA. PCNA ubiquitination prevents genomic instability from stalled replication forks after DNA damage. |
| SIAH1 | β-catenin, Bim, TRB3 | SIAH1 is an E3 ubiquitin ligase that plays a role in inhibition of Wnt signaling through ubiquitination of β-catenin. SIAH1 has also been shown to promote apoptosis through upregulation of Bim, and to ubiquitinate the signaling adaptor protein TRB3. |
| SIAH2 | HIPK2, PHD1/3 | SIAH2 is an E3 ubiquitin ligase that plays a role in hypoxia through ubiquitination and degradation of HIPK2. SIAH2 also ubiquitinates PHD1/3, which regulates levels of HIF-1α in response to hypoxia. |
| SMURF1 | Smads | SMURF1 is an E3 ubiquitin ligase that interacts with BMP pathway Smad effectors, leading to Smad protein ubiquitination and degradation. Smurf1 negatively regulates osteoblast differentiation and bone formation in vivo. |
| SMURF2 | Smads, Mad2 | SMURF2 is an E3 ubiquitin ligase that interacts with Smads from both the BMP and TGF-β pathways. SMURF2 also regulates the mitotic spindle checkpoint through ubiquitination of Mad2. |
| TOPORS | p53, NKX3.1 | TOPORS is an E3 ubiquitin ligase and a SUMO ligase. TOPORS ubiquitinates and sumoylates p53, which regulates p53 stability. TOPORS has also been shown to ubiquitinate the tumor supressor NKX3.1. |
| TRAF6 | NEMO, Akt1 | TRAF6 is an E3 ubiquitin ligase that functions as an adaptor protein in IL-1R, CD40, and TLR signaling. TRAF6 promotes NF-κB signaling through K63 polyubiquitination of IKK, resulting in IKK activation. TRAF6 has also been shown to ubiquitinate Akt1, causing its translocation to the cell membrane. |
| TRAF7 | | TRAF7 is an E3 ubiquitin ligase and SUMO ligase that functions as an adaptor protein in TNF Receptor and TLR signaling. TRAF7 has been shown to be capable of self-ubiquitination and plays a role in apoptosis via MEKK3-mediated activation of NF-κB. |
| TRIM63 | Troponin I, MyBP-C, MyLC1/2 | TRIM63 is also known as Murf-1. TRIM63 is a muscle-specific E3 ubiquitin ligase whose expression is upregulated during muscle atrophy. TRIM63 has been shown to ubiquitinate several important muscle proteins including troponin I, MyBP-C, and MyLC1/2. |
| UBE3B | | UBE3B is an E3 ubiquitin ligase identified through sequence analysis. The specific substrates and cellular function of UBE3B is currently unknown. |
| UBE3C | | UBE3C is an E3 ubiquitin ligase also known as KIAA10. UBE3C is highly expressed in muscle and may interact with the transcriptional regulator TIP120B. |

TABLE 2-continued

| Ligase | Substrate | Function |
| --- | --- | --- |
| UBR1 | | UBR1 is an E3 ubiquitin ligase responsible for proteasomal degradation of misfolded cytoplasmic proteins. UBR1 has also been shown to be a ubiquitin ligase of the N-end rule proteolytic pathway, which regulates degradation of short-lived proteins. |
| UBR2 | Histone H2A | UBR2 is an E3 ubiquitin ligase that has been shown to ubiquitinate histone H2A, resulting in transcriptional silencing. UBR2 is also part of the N-end rule proteolytic pathway. |
| UHRF2 | PCNP | UHRF2 is also known as NIRF. UHRF2 is a nuclear protein that may regulate cell cycle progression through association with Chk2. UHRF2 also ubiquitinates PCNP and has been shown to play a role in degradation of nuclear aggregates containing polyglutamine repeats. |
| VHL | HIF-1α | VHL is the substrate recognition component of the ECV (Elongin B/C, Cullen-2, VHL) E3 ubiquitin ligase complex responsible for degradation of the transcription factor HIF-1α. Ubiquitination and degradation of HIF-1α takes place only during periods of normoxia, but not during hypoxia, thereby playing a central role in the regulation of gene expression by oxygen. |
| WWP1 | ErbB4 | WWP1 is an E3 ubiquitin ligase commonly found to be overexpressed in breast cancer. WWP1 has been shown to ubiquitinate and degrade ErbB4. Interestingly, the WWP1 homolog in *C. elegans* was found to increase life expectancy in response to dietary restriction. |
| WWP2 | Oct-4 | WWP2 is an E3 ubiquitin ligase that has been shown to ubiquitinate/degrade the stem cell pluripotency factor Oct-4. WWP2 also ubiquitinates the transcription factor EGR2 to inhibit activation-induced T cell death. |
| ZNRF1 | | ZNRF1 is an E3 ubiquitin ligase highly expressed in neuronal cells. ZNRF1 is found in synaptic vesicle membranes and may regulate neuronal transmissions and plasticity. |

The term "deubiquitinating" enzyme refers to an enzyme that cleaves ubiquitin from proteins.

According to a specific embodiment, the deubiquitinating enzyme is a cysteine protease or a metalloprotease.

Exemplary deubiquitinating enzymes which may be expressed in the system include USP7 that is known to deubiquitinate MDM2, USP47, USP2, USP7, USP15, USP9X, USP28, USP30.

The ubiquitinating or deubiquitinating enzymes may be expressed from the same expression constructs as the substrate and the ubiquitin or on separate constructs.

The reporter protein fragments and one or more members of the putative binding pair are generally linked either directly or via a linker, and are generally linked by a covalent linkage. For example, when the reporter protein fragment and the members of the putative binding pair are proteins, they may be linked by methods known in the art for linking peptides.

The fragment members of reporter proteins also may include a flexible polypeptide linker separating the fragment of reporter protein from the member of the putative binding pair and allowing for their independent folding. The linker is optimally 15 amino acids or 60 angstroms in length (about 4 angstroms per residue) but may be as long as 30 amino acids but preferably not more than 20 amino acids in length. It may be as short as 3 amino acids in length, but more preferably is at least 6 amino acids in length. To ensure flexibility and to avoid introducing steric hindrance that may interfere with the independent folding of the fragment domain of reporter protein and the members of the putative binding pair, the linker should be comprised of small, preferably neutral residues such as Gly, Ala, and Val, but also may include polar residues that have heteroatoms such as Ser and Met, and may also contain charged residues.

The present inventors further contemplate that the N and C fragments are encoded on a single nucleic acid.

Thus according to another aspect of the present invention there is provided an isolated polynucleotide comprising:

(i) a first nucleic acid sequence that encodes an N-terminal fragment of chloramphenicol acetyl transferase (CAT), wherein said first nucleic acid sequence comprises a stop codon positioned in the catalytic active site encoding sequence of the CAT; and (ii) a second nucleic acid sequence that encodes a C terminal fragment of said CAT, wherein said second nucleic acid sequence comprises a start codon positioned in the catalytic active site encoding sequence of the CAT, and wherein said N-terminal fragment is capable of associating with said C-terminal fragment to generate an active CAT that is capable of acetylating chloramphenicol.

Appropriate host cells for application of the present invention are prokaryotic host cells, such as bacterial cells. In a preferred embodiment, the host cell is a gram-negative bacteria. Host cells suitable for expressing the proteins of the present invention include any one of the more commonly available gram-negative bacteria. Suitable microorganisms include *Pseudomonas aeruginosa, Escherichia coli, Salmonella gastroenteritis (typhimirium), S. typhi, S. enteriditis, Shigella flexneri, S. sonnie, S. dysenteriae, Neisseria gonorrhoeae, N. meningitides, Haemophilus influenzae H. pleuropneumoniae, Pasteurella haemolytica, P. multilocida, Legionella pneumophila, Treponema pallidum, T. denticola, T. orales, Borrelia burgdorferi, Borrelia* spp. *Leptospira interrogans, Klebsiella pneumoniae, Proteus vulgaris, P. morganii, P. mirabilis, Rickettsia prowazeki, R. typhi, R. richettsii, Porphyromonas (Bacteriodes) gingivalis, Chlamydia psittaci, C. pneumoniae, C. trachomatis, Campylobacter jejuni, C. intermedis, C. fetus, Helicobacter pylori, Francisella tularenisis, Vibrio cholerae, Vibrio parahaemolyticus, Bordetella pertussis, Burkholderie pseudomallei, Brucella abortus, B. susi, B. melitensis, B. canis, Spirillum minus, Pseudomonas mallei, Aeromonas hydrophile, A. salmonicida,* and *Yersinia pestis*. Methods for transforming/transfecting host cells with expression vectors are well-known in the art and depend on the host system selected as described in Sambrook et al., Molecular Cloning: A Laboratory Manual, Cold Springs Laboratory Press, Cold Springs Harbor, N.Y. (1989), which is hereby incorporated by reference in its entirety.

The present invention further contemplates cell cultures comprising bacterial cells which have been transformed with any of the constructs described herein. Preferably, the cell cultures further comprise media which allow for the propagation of the cells and maintain the cells viable. The cell culture may further comprise chloramphenicol.

As will be apparent to one of skill in the art, the present invention allows for a broad range of studies of protein-protein and other types of multi-protein interactions to be carried out quantitatively or qualitatively in prokaryotic host cells. The proteins of the present invention could be endogenous prokaryotic proteins or a heterologous/eukaryotic proteins. In what follows, non-limiting examples of different applications of the invention are provided.

Another aspect of the present invention relates to a method of identifying a candidate protein which binds a target protein. This method includes providing a first construct system comprising a nucleic acid molecule encoding a first fragment (e.g. the N fragment) of the CAT, and a nucleic acid molecule encoding a target protein, where the nucleic acid molecule encoding the first fragment and the nucleic acid molecule encoding the target protein are operatively coupled to permit their expression in a prokaryotic host cell as a first fusion protein. This method also includes providing a second construct system comprising a nucleic acid molecule encoding a second fragment of the CAT molecule (e.g. the C fragment) and a nucleic acid molecule encoding a candidate protein, wherein the nucleic acid molecule encoding the second fragment and the nucleic acid molecule encoding the candidate protein are operatively coupled to permit their expression in a prokaryotic host cell as a second fusion protein. This method further includes transforming a prokaryotic host cell with the first expression system and the second expression system, culturing the transformed prokaryotic host cell under conditions effective to express the first and the second fusion proteins in the cytoplasm of the cell. The prokaryotic host cells with reporter protein molecule activity are detected as those where binding between the candidate protein and the target protein has occurred. The candidate protein is identified as having the ability to bind to the target protein based on whether the host cell has reporter protein activity. Cells which are able to survive in the presence of chloramphenicol are those that express an active CAT protein. The proteins that can be used as target proteins and candidate proteins are mentioned supra.

The construct systems of the present invention can be used in many applications such as in human therapeutics, diagnostics, and prognostics, in high-throughput screening systems for the discovery and validation of pharmaceutical targets and drugs, as well as discovery of genes that modulate protein interactions. Massive parallel mapping of pairwise protein-protein interactions within and between the proteomes of cells, tissues, and pathogenic organisms, selection of antibody fragments or other binding proteins to whole proteomes, antigen identification for antibodies, epitope identification for antibodies, high-throughput screens for inhibitors of any protein-protein interaction can be done using the methods of the present invention. In one embodiment, the construct system can be combined with directed evolution methods and used to engineer ultra-high affinity interactions between proteins such as antibody-antigen pairs.

By combining the methods and compositions of the invention with state-of-the-art methods for construction of high-titer, high-complexity cDNA libraries, it will be possible to identify interaction partners of a specific test protein from, for example, mammalian cells (i.e., perform functional genomics at the protein level). For this application, cDNA libraries can be constructed wherein the cDNA coding sequence is fused to a sequence encoding the reporter protein fragments of the present invention. A sequence encoding a binding protein of interest will be fused to a reporter protein fragment in a first vector. In a second series of vectors, a second reporter protein fragment will be fused to a variety of different proteins that will be tested for their ability to bind to the protein of interest. Testing will be conducted by co-transformation of prokaryotic host cells with the first and one of the series of second vectors. Those test proteins which are capable of binding to the protein of interest will allow cells in which they are co-expressed with the protein of interest to survive in the presence of chloramphenicol.

This aspect of the present invention, the method can be separately carried out with a plurality of second expression systems containing a plurality of different nucleic acid molecules encoding different second proteins. This plurality of different second proteins can be encoded by members of a cDNA library. The methods of the present invention could be adapted for efficient simultaneous detection of multitudes of interactions among proteins within cells, including expressed sequence libraries, cDNA libraries, single-chain antibody fragment (scFv) libraries, and scaffolded peptide libraries. They could also be used for rapid selection of binding molecules from single-chain antibody fragment (scFv) libraries, or from scaffolded peptide libraries for use as reagents in functional genomics studies, or for identification of natural ligands and epitopes by homology. Target interactions identified using the present invention, could be used immediately to screen for candidate compounds that act as inhibitors or activators of the protein-protein interaction.

In one embodiment of this aspect of the invention, the reporter protein molecule activity can be quantitated. In a preferred embodiment, the reporter protein activity detected among various candidate proteins is compared and used to identify the strongest binding candidate protein. This comparison among the plurality of candidate proteins can also be used to determine which of a plurality of candidate proteins bind to the target protein, or to rank the candidate proteins according to their binding affinities.

This application will also be useful in screening for agonists and antagonists of medically-relevant protein interactions. The assays and methods of the invention can also be carried out in the presence of extracellular signaling molecules, growth factors or differentiation factors, activated or inactivated genes or signals, peptides, organic compounds, drugs or synthetic analogs, or the like, whose presence or effects might alter the potential for interaction between the target protein and the candidate protein.

In one embodiment, the application is useful for screening for substrates of a ubiquitinating enzyme.

Any bacteria can be used for this assay so long as it lacks endogenous deubiquitinase activity and preferably also endogenous ubitquitinase activity. In one embodiment, the bacteria has at least 10 fold less endogenous deubiquitinase activity and endogenous ubiquitinase activity than a human cell. In another embodiment, the bacteria has at least 20 fold less endogenous deubiquitinase activity and endogenous ubiquitinase activity than a human cell.

Preferably the bacteria lack resistance to the selection markers in the current system. Examples of such bacteria include, but are not limited to *E. coli* K-12 derivatives including W3110, MG1655, DH5α, JM101, JM19, BL21, B834, XL1-Blue; also other non *E. coli* bacteria maybe used.

According to a particular embodiment, the bacteria used in the system are of the genus *Escherichia*, such as for example *E. Coli*.

Another aspect of the present invention relates to a method of identifying an agent which regulates (i.e. modulates) the binding of a first test polypeptide to a second test polypeptide.

This method includes providing a first construct system comprising a nucleic acid molecule encoding a first fragment of a CAT molecule (e.g. N fragment) and a nucleic acid molecule encoding a first protein, where the nucleic acid molecule encoding the first fragment and the nucleic acid molecule encoding the first protein are operatively coupled to permit their expression in a prokaryotic host cell as a first fusion protein. This method also includes providing a second construct system for expressing the second protein comprising a nucleic acid molecule encoding a second fragment of the reporter protein molecule (e.g. C fragment) and a nucleic acid molecule encoding a second protein, where the nucleic acid molecule encoding the second fragment, the nucleic acid molecule encoding the second signal sequence, and the nucleic acid molecule encoding the second protein are operatively coupled to permit their expression in a prokaryotic host cell as a second fusion protein. This method further involves providing an agent to the prokaryotic host cell (e.g. providing a nucleic acid which encodes the agent in a form suitable for expression in a prokaryotic host cell) transforming the prokaryotic host cell with the first expression system, the second expression system, and the candidate agent, and culturing the transformed prokaryotic host cell under conditions effective to express the first fusion protein, the second fusion protein, and the agent. Any reporter activity in the transformed prokaryotic host cell is detected, and prokaryotic host cells, with reporter activity that is different than that achieved without transformation of the agent are identified, as containing an agent which modulates binding between the first and second proteins.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Based on the crystal structure of $CAT_I$ in its apo and complex with chloramphenicol (PDB accessions 3U9B and 3U9F), a split-CAT system was designed that permits PPI studies in chloramphenicol sensitive bacteria such as E. coli K-12. The crystal structure of $CAT_I$ shows that the enzyme assembles into a homo-trimeric structure (FIG. 1). The N-termini of each of protomers cover the catalytic active site pocket of the neighboring protomer. A split-CAT system was constructed where the N-terminus fragment residues 1-30 was fused in frame downstream to one protein of interest (protein A of the A:B complex; FIGS. 2A-C); and the C-terminus fragment of the split CAT was fused to the second protein of interest (protein B of the A:B complex). The proteins of interest (A and B) were fused in front of the N-CAT fragment and downstream to the C-CAT. Moreover, to express the C-terminus fragment (a.a. 31-219) an initiation codon (ATG) is needed. This additional formyl-methionine (in E. coli) may severely interfere with active site arrangement and catalysis (FIG. 3). However, since a small residue (Cys31) is located immediately after the formyl-methionine the latter is post-translationally removed from the N-terminus (of the C-terminus fragment) hence salvaging the active site arrangement as seen by the activity (FIGS. 4A-C). To assess the split protein, a well characterized PPI non-covalent complex namely ESCRT-0 of yeast was selected as the testing model. The yeast ESCRT-0 core complex consists of two coiled-coil intertwined GAT domains from of Vps27 and Hse1 proteins. The crystal structure of the complex was determined and structural based point mutations at the PPI interface were characterized (Prag et al., 2007). In-frame Vps27 and Hse1 were tethered to N- and the C-CAT fragments (respectively) using long flexible linkers (Levin-Kravets et al., 2016). As shown in FIG. 4B when wild-type Vps27 and Hse1 GAT domain are fused and expressed in the selection system growth phenotype was clearly observed. Removal of ether the Vps27-nCAT or the Hse1-cCAT resulted in clear growth arrest phenotypes. Similarly, replacing the Hse1 GAT domain with ubiquitin (Ub) did not yield growth under the selective conditions. Importantly, under non-selective conditions all the bacterial variants presented identical growth phenotypes. To further assess this PPI in the newly designed selection system, point mutations were introduced at the Vps27:Hse1 non-covalent binding interface [FIG. 4A; (Prag et al., 2007)]. While L410D and I420D mutants presented severe growth arrest phenotypes, the positive control mutation, L437D mutation, (which is not located at the binding interface), showed a wild-type phenotype.

Figure 6A:
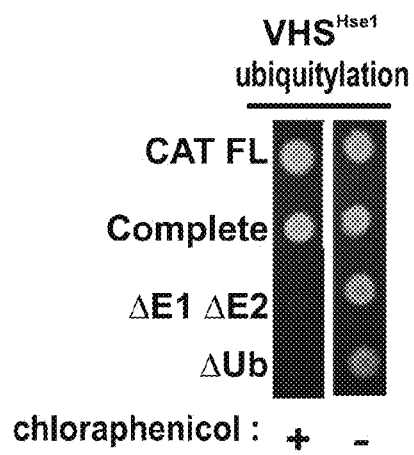

To test if the newly designed split-CAT system functions with ubiquitylation cascades, a ubiquitylation target was tethered to the nCAT fragment and Ub to the cCAT fragment (FIG. 5). The fused proteins were co-expressed with their cognate ubiquitylation apparatus and bacteria were spotted on selective media (rich agar supplemented with 7-10 mg of chloramphenicol per ml). At first, a simple ubiquitylation cascade which consists of the Ub-receptor (an Ub-Binding Domain UBD containing protein) as ubiquitylation target was tested. It has been demonstrated that many UBDs undergoes E3-independent ubiquitylation (Hoeller et al., 2007). The present inventors therefore co-expressed the Ub-receptor of Hse1-VHS domain tethered to the nCAT (Levin-Kravets et al., 2016; Ren and Hurley, 2010) and nCAT-Ub with wheat E1 (Uba1) and the yeast E2 (Ubc4). As shown in FIG. 6A expression of complete ubiquitylation cascade of VHS domain tethered to the split-CAT system presented growth phenotype. However, when the ubiquitylation enzymes E1 and E2 or Ub were removed growth arrest phenotypes were found.

Figure 6B:
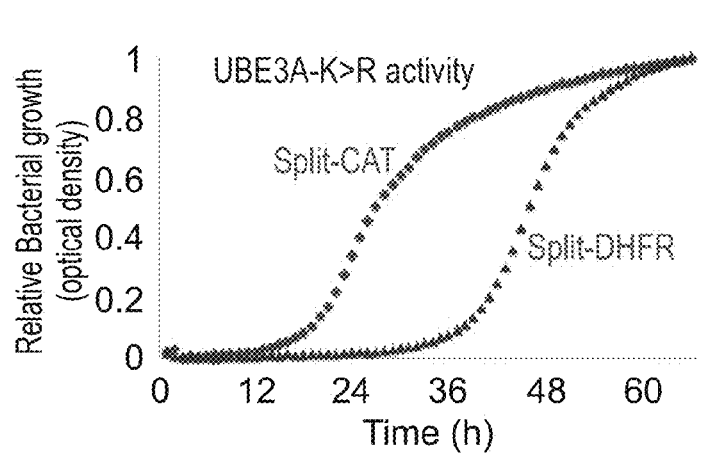

To compare the growth efficiency between the split-DHFR vs. the split-CAT systems a UBE3A (also known as E6AP) Rpn10 ubiquitylation dependent cascade was constructed in both systems. It has been previously demonstrated a self-ubiquitylation dependent allosteric mechanism that restrains Nedd4 family members (Attali et al., 2017). Based on this study the present inventors recently characterized identical mechanism within UBE3A and constructed a K>R mutation that results in a constitutive hyperactive E3-ligase. They co-expressed the ligase from the same $3^{rd}$ E3-ligase. They co-expressed the ligase from the same 3rd vector under the regulation of the leaky promoter pTac (i.e. without the addition of IPTG) in bacteria that express Ub, Rpn10, Uba1 (E1) and UBCH7 (E2). FIG. 6B shows a significant difference in growth efficiency between the two systems.

Figure 6C:
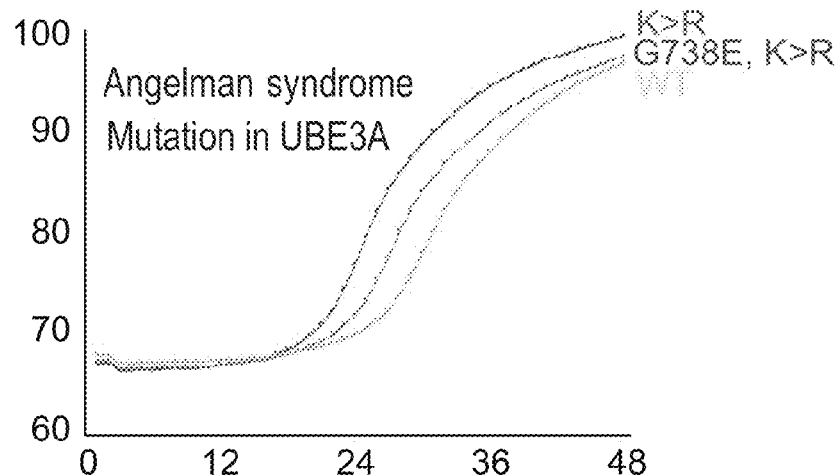
Figure 6D:
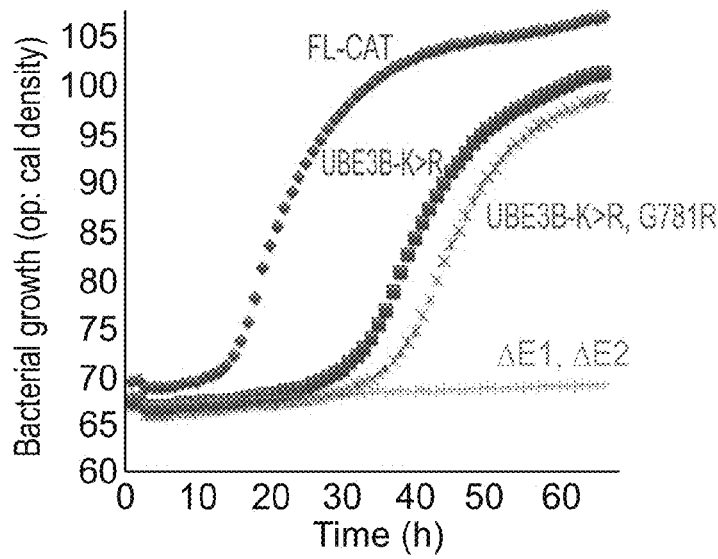

To demonstrate the system application to study the effect of point mutations an Angelman syndrome (AS) mutation was introduced into UBE3A and the bacterial growth in wild-type (self-arrested), K>R mutant (hyperactive) and AS mutation was monitored on the background of the K>R mutation (FIG. 6C). It was found that the K>R mutation resulted in a higher efficient growth phenotype while the AS mutation resulted in a decreased efficient growth phenotype compare with the WT enzyme. Similarly, the function of UBE3B a HECT E3 Ub-ligase that presents a difficulty in purification in its active from and involve in Kaufman Syndrome (KS; Flex et al. 2013) was also assessed in the developed system. Using the selection system, the present inventors identified the critical lysine residue that undergoes self-ubiquitylation that lead to allosteric restrain of the enzyme and constructed a K>R unrestraint mutant. KS mutation on the background of the UBE3B K>R demonstrated a growth phenotype (FIG. 6D).

The current results with the ubiquitylation cascades and UBDs suggest that affinity between UBD and Ub at ~180 µM is insufficient to promote growth without ubiquitylation (FIGS. 6A-D). It is now suggested that tethering ubiquitylation cascade to PPI can stabilize transient weak interaction in the bacteria. Furthermore, the present inventors suggest that co-expression of two PPI along with ubiquitylation cascade where Ub is tethered downstream to one of the two PPI components would results in ubiquitylation of the second component of the PPI (as depicted in FIG. 7). Therefore, one can employ the split-CAT genetic selection system to identify and characterize ultra-weak PPI in given proteomes.

REFERENCES

Attali, I., Tobelaim, W. S., Persaud, A., Motamedchaboki, K., Simpson-Lavy, K. J., Mashahreh, B., Levin-Kravets, O., Keren-Kaplan, T., Pilzer, I., Kupiec, M., et al. (2017). Ubiquitylation-dependent oligomerization regulates activity of Nedd4 ligases. The EMBO journal 36, 425-440.

Flex, E., Ciolfi, A., Caputo, V., Fodale, V., Leoni. C., Melis, D., Bedeschi. M. F., Mazzanti. L., Pizzuti, A., Tartaglia, M., and Zampino, G. (2013). Loss of function of the E3 ubiquitin-protein ligase UBE3B causes Kaufman oculocerebrofacial syndrome. J Med Genet. 50, 493-499

Hoeller, D., Hecker, C. M., Wagner, S., Rogov, V., Dotsch, V., and Dikic, I. (2007). E3-independent monoubiquitination of ubiquitin-binding proteins. Mol Cell 26, 891-898.

Levin-Kravets, O., Tanner, N., Shohat, N., Attali, I., Keren-Kaplan, T., Shusterman, A., Artzi, S., Varvak, A., Reshef, Y., Shi, X., et al. (2016). A bacterial genetic selection system for ubiquitylation cascade discovery. Nature methods 13, 945-952.

Pelletier, J. N., Campbell-Valois, F. X., and Michnick, S. W. (1998). Oligomerization domain-directed reassembly of active dihydrofolate reductase from rationally designed fragments. Proc Natl Acad Sci USA 95, 12141-12146.

Prag, G., Watson, H., Kim, Y. C., Beach, B. M., Ghirlando, R., Hummer, G., Bonifacino, J. S., and Hurley, J. H. (2007). The Vps27/Hse1 complex is a GAT domain-based scaffold for ubiquitin-dependent sorting. Developmental cell 12, 973-986.

Ren, X., and Hurley, J. H. (2010). VHS domains of ESCRT-0 cooperate in high-avidity binding to polyubiquitinated cargo. The EMBO journal 29, 1045-1054.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A construct system comprising:
   (i) a first nucleic acid construct comprising a first polynucleotide having a nucleic acid sequence that encodes a N-terminal fragment of chloramphenicol acetyl transferase (CAT), said N-terminal fragment comprising a first portion of the catalytic active site of said CAT, said N-terminal fragment being devoid of acetylating activity; and
   (ii) a second nucleic acid construct comprising a second polynucleotide having a nucleic acid sequence that encodes a C terminal fragment of said CAT, said C-terminal fragment comprising a second portion of the catalytic active site of said CAT, said C-terminal fragment being devoid of acetylating activity; and
   wherein said N-terminal fragment is capable of associating with said C-terminal fragment to generate an active CAT that is capable of acetylating chloramphenicol,
   wherein said N terminal fragment consists of the amino acid sequence as set forth in SEQ ID NO: 2 or 6; and/or
   said C-terminal fragment consists of the amino acid sequence as set forth in SEQ ID NOs: 3 or 7.

2. The system of claim 1, wherein
   (i) said first polynucleotide further comprises a cloning site, wherein a position of said cloning site is selected such that upon insertion of a polynucletide having a sequence which encodes a test polypeptide into said cloning site, following expression in a cell, a fusion protein is generated which comprises said test polypeptide in frame with said N-terminal fragment; or
   (ii) said second polynucleotide further comprises a cloning site, wherein a position of said cloning site is selected such that upon insertion of a polynucleotide having a sequence which encodes a test polypeptide into said cloning site, following expression in a cell, a fusion protein is generated which comprises said test polypeptide in frame with said C-terminal fragment.

3. The system of claim 1, wherein said first and said second nucleic acid constructs comprise a bacterial origin of replication.

4. The system of claim 1, wherein said first nucleic acid construct further comprises a nucleic acid sequence that encodes a first test polypeptide at a position such that, following expression in a cell, a fusion protein is generated which comprises said test polypeptide in frame with said N-terminal fragment.

5. The system of claim 4, wherein said second nucleic acid construct further comprises a nucleic acid sequence that encodes a second test polypeptide at a position such that, following expression in a cell, a fusion protein is generated which comprises said test polypeptide in frame with said C-terminal fragment.

6. The system of claim 4, wherein said second nucleic acid construct further comprises a nucleic acid sequence that encodes a second test polypeptide, which is non-identical to said first test polypeptide, at a position such that, following expression in a cell, a second fusion protein is generated which comprises said second test polypeptide in frame with said C-terminal fragment.

7. The system of claim 4, wherein said test polypeptide is ubiquitin.

8. The system of claim 7, wherein said first nucleic acid construct or said second nucleic acid construct further encode at least one ubiquitinating enzyme.

9. The system of claim 7, further comprising a third nucleic acid construct having a nucleic acid sequence that encodes at least one ubiquitinating enzyme.

10. The system of claim 1, wherein said N-terminal fragment is encoded by the nucleic acid sequence as set forth in SEQ ID NO: 4.

11. The system of claim 1, wherein said C-terminal fragment is encoded by the nucleic acid sequence as set forth in SEQ ID NO: 5.

12. A cell population which express the system of claim 1.

13. A method of determining whether a first test polypeptide binds to a second test polypeptide comprising:
   (a) expressing the system of claim 6 in a population of cells in a medium comprising chloramphenicol; and subsequently (b) analyzing survival of said cells, wherein the survival of a cell in said population of cells is indicative that said first test polypeptide has bound to said second test polypeptide in said cell.

14. The method of claim 13, wherein said first test polypeptide or said second test polypeptide is ubiquitin.

\* \* \* \* \*

SEQUENCE LISTING

```
<160> NUMBER OF SEQ ID NOS: 11

<210> SEQ ID NO 1
<211> LENGTH: 219
<212> TYPE: PRT
<213> ORGANISM: Escherichia coli

<400> SEQUENCE: 1

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
                20                  25                  30

Tyr Asn Gln Thr Val Gln Leu Asp Ile Thr Ala Phe Leu Lys Thr Val
            35                  40                  45

Lys Lys Asn Lys His Lys Phe Tyr Pro Ala Phe Ile His Ile Leu Ala
        50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
                100                 105                 110

Phe Arg Gln Phe Leu His Ile Tyr Ser Gln Asp Val Ala Cys Tyr Gly
            115                 120                 125

Glu Asn Leu Ala Tyr Phe Pro Lys Gly Phe Ile Glu Asn Met Phe Phe
        130                 135                 140

Val Ser Ala Asn Pro Trp Val Ser Phe Thr Ser Phe Asp Leu Asn Val
145                 150                 155                 160

Ala Asn Met Asp Asn Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205
```

```
Gln Gln Tyr Cys Asp Glu Trp Gln Gly Gly Ala
    210                 215
```

<210> SEQ ID NO 2
<211> LENGTH: 30
<212> TYPE: PRT
<213> ORGANISM: Artificial sequence
<220> FEATURE:
<223> OTHER INFORMATION: CAT N terminal protein sequence

<400> SEQUENCE: 2

```
Met Glu Lys Lys Ile Thr Gly Tyr Thr Thr Val Asp Ile Ser Gln Trp
1               5                   10                  15
His Arg Lys Glu His Phe Glu Ala Phe Gln Ser Val Ala Gln
            20                  25                  30
```

<210> SEQ ID NO 3
<211> LENGTH: 190
<212> TYPE: PRT
<213> ORGANISM: Artificial sequence
<220> FEATURE:
<223> OTHER INFORMATION: CAT C terminal protein sequence

<400> SEQUENCE: 3

```
Met Cys Thr Tyr Asn Gln Thr Val Gln Leu Asp Ile Thr Ala Phe Leu
1               5                   10                  15

Lys Thr Val Lys Lys Asn Lys His Lys Phe Tyr Pro Ala Phe Ile His
            20                  25                  30

Ile Leu Ala Arg Leu Met Asn Ala His Pro Glu Phe Arg Met Ala Met
        35                  40                  45

Lys Asp Gly Glu Leu Val Ile Trp Asp Ser Val His Pro Cys Tyr Thr
    50                  55                  60

Val Phe His Glu Gln Thr Glu Thr Phe Ser Ser Leu Trp Ser Glu Tyr
65                  70                  75                  80

His Asp Asp Phe Arg Gln Phe Leu His Ile Tyr Ser Gln Asp Val Ala
                85                  90                  95

Cys Tyr Gly Glu Asn Leu Ala Tyr Phe Pro Lys Gly Phe Ile Glu Asn
            100                 105                 110

Met Phe Phe Val Ser Ala Asn Pro Trp Val Ser Phe Thr Ser Phe Asp
        115                 120                 125

Leu Asn Val Ala Asn Met Asp Asn Phe Phe Ala Pro Val Phe Thr Met
    130                 135                 140

Gly Lys Tyr Tyr Thr Gln Gly Asp Lys Val Leu Met Pro Leu Ala Ile
145                 150                 155                 160

Gln Val His His Ala Val Cys Asp Gly Phe His Val Gly Arg Met Leu
                165                 170                 175

Asn Glu Leu Gln Gln Tyr Cys Asp Glu Trp Gln Gly Gly Ala
            180                 185                 190
```

<210> SEQ ID NO 4
<211> LENGTH: 93
<212> TYPE: DNA
<213> ORGANISM: Artificial sequence
<220> FEATURE:
<223> OTHER INFORMATION: CAT N terminal DNA sequence

<400> SEQUENCE: 4

```
atggagaaaa aaatcactgg atataccacc gttgatatat cccaatggca tcgtaaagaa      60
cattttgagg catttcagtc agttgctcaa taa                                    93
```

<210> SEQ ID NO 5
<211> LENGTH: 573
<212> TYPE: DNA
<213> ORGANISM: Artificial sequence
<220> FEATURE:
<223> OTHER INFORMATION: CAT C terminal DNA sequence

<400> SEQUENCE: 5

```
atgtgtacct ataaccagac cgttcagctg gatattacgg cctttttaaa gaccgtaaag      60
aaaaataagc acaagtttta tccggccttt attcacattc ttgcccgcct gatgaatgct     120
catccggaat ccgtatggc aatgaaagac ggtgagctgg tgatatggga tagtgttcac     180
ccttgttaca ccgttttcca tgagcaaact gaaacgtttt catcgctctg gagtgaatac     240
cacgacgatt tccggcagtt tctacacata tattcgcaag atgtggcgtg ttacggtgaa     300
aacctggcct atttccctaa agggtttatt gagaatatgt ttttcgtctc agccaatccc     360
tgggtgagtt tcaccagttt tgatttaaac gtggccaata tggacaactt cttcgccccc     420
gttttcacca tggcaaata ttatacgcaa ggcgacaagg tgctgatgcc gctggcgatt     480
caggttcatc atgccgtctg tgatggcttc catgtcggca gaatgcttaa tgaattacaa     540
cagtactgcg atgagtggca gggcggggcg taa                                  573
```

<210> SEQ ID NO 6
<211> LENGTH: 28
<212> TYPE: PRT
<213> ORGANISM: Artificial sequence
<220> FEATURE:
<223> OTHER INFORMATION: CAT N terminal protein sequence

<400> SEQUENCE: 6

```
Met Glu Lys Lys Ile Thr Gly Tyr Thr Thr Val Asp Ile Ser Gln Trp
1               5                   10                  15
His Arg Lys Glu His Phe Glu Ala Phe Gln Ser Val
            20                  25
```

<210> SEQ ID NO 7
<211> LENGTH: 192
<212> TYPE: PRT
<213> ORGANISM: Artificial sequence
<220> FEATURE:
<223> OTHER INFORMATION: CAT C terminal protein sequence

<400> SEQUENCE: 7

```
Met Ala Gln Cys Thr Tyr Asn Gln Thr Val Gln Leu Asp Ile Thr Ala
1               5                   10                  15
Phe Leu Lys Thr Val Lys Lys Asn Lys His Lys Phe Tyr Pro Ala Phe
                20                  25                  30
Ile His Ile Leu Ala Arg Leu Met Asn Ala His Pro Glu Phe Arg Met
            35                  40                  45
Ala Met Lys Asp Gly Glu Leu Val Ile Trp Asp Ser Val His Pro Cys
        50                  55                  60
Tyr Thr Val Phe His Glu Gln Thr Glu Thr Phe Ser Ser Leu Trp Ser
65                  70                  75                  80
Glu Tyr His Asp Asp Phe Arg Gln Phe Leu His Ile Tyr Ser Gln Asp
                85                  90                  95
Val Ala Cys Tyr Gly Glu Asn Leu Ala Tyr Phe Pro Lys Gly Phe Ile
            100                 105                 110
Glu Asn Met Phe Phe Val Ser Ala Asn Pro Trp Val Ser Phe Thr Ser
        115                 120                 125
```

```
Phe Asp Leu Asn Val Ala Asn Met Asp Asn Phe Phe Ala Pro Val Phe
        130                 135                 140
Thr Met Gly Lys Tyr Tyr Thr Gln Gly Asp Lys Val Leu Met Pro Leu
145                 150                 155                 160
Ala Ile Gln Val His His Ala Val Cys Asp Gly Phe His Val Gly Arg
                165                 170                 175
Met Leu Asn Glu Leu Gln Gln Tyr Cys Asp Glu Trp Gln Gly Gly Ala
            180                 185                 190
```

<210> SEQ ID NO 8
<211> LENGTH: 660
<212> TYPE: DNA
<213> ORGANISM: Escherichia coli

<400> SEQUENCE: 8

```
atggagaaaa aaatcactgg atataccacc gttgatatat cccaatggca tcgtaaagaa      60
cattttgagg catttcagtc agttgctcaa tgtacctata accagaccgt tcagctggat     120
attacggcct tttaaagac cgtaaagaaa ataagcaca gtttatcc ggcctttat          180
cacattcttg cccgcctgat gaatgctcat ccggaattcc gtatggcaat gaaagacggt     240
gagctggtga tatgggatag tgttcaccct tgttacaccg ttttccatga gcaaactgaa     300
acgttttcat cgctctggag tgaataccac gacgatttcc ggcagtttct acacatatat     360
tcgcaagatg tggcgtgtta cggtgaaaac ctggcctatt ccctaaaagg gtttattgag     420
aatatgtttt tcgtctcagc caatccctgg gtgagtttca ccagttttga tttaaacgtg     480
gccaatatgg acaacttctt cgcccccgtt ttcaccatgg gcaaatatta tacgcaaggc     540
gacaaggtgc tgatgccgct ggcgattcag gttcatcatg ccgtctgtga tggcttccat     600
gtcggcagaa tgcttaatga attacaacag tactgcgatg agtggcaggg cggggcgtaa    660
```

<210> SEQ ID NO 9
<211> LENGTH: 76
<212> TYPE: PRT
<213> ORGANISM: Artificial sequence
<220> FEATURE:
<223> OTHER INFORMATION: mammalian ubiquitin protein sequence

<400> SEQUENCE: 9

```
Met Gln Ile Phe Val Lys Thr Leu Thr Gly Lys Thr Ile Thr Leu Glu
1               5                   10                  15
Val Glu Pro Ser Asp Thr Ile Glu Asn Val Lys Ala Lys Ile Gln Asp
            20                  25                  30
Lys Glu Gly Ile Pro Pro Asp Gln Gln Arg Leu Ile Phe Ala Gly Lys
        35                  40                  45
Gln Leu Glu Asp Gly Arg Thr Leu Ser Asp Tyr Asn Ile Gln Lys Glu
    50                  55                  60
Ser Thr Leu His Leu Val Leu Arg Leu Arg Gly Gly
65                  70                  75
```

<210> SEQ ID NO 10
<211> LENGTH: 75
<212> TYPE: PRT
<213> ORGANISM: Artificial sequence
<220> FEATURE:
<223> OTHER INFORMATION: yeast ubiquitin protein sequence

<400> SEQUENCE: 10

```
Met Gln Ile Phe Val Lys Thr Leu Thr Gly Lys Thr Ile Thr Leu Glu
1               5                   10                  15
```

```
Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Leu Ser Asp Tyr Asn Ile Gln Lys Glu Ser
    50                  55                  60

Thr Leu His Leu Val Leu Arg Leu Arg Gly Gly
65                  70                  75

<210> SEQ ID NO 11
<211> LENGTH: 18
<212> TYPE: PRT
<213> ORGANISM: Artificial Sequence
<220> FEATURE:
<223> OTHER INFORMATION: Amino acid sequence of the active site of CAT

<400> SEQUENCE: 11

Ala Phe Gln Ser Val Ala Gln Cys Thr Tyr Asn Gln Thr Val Gln Leu
1               5                   10                  15

Asp Ile
```